(12) United States Patent
Bohlmann et al.

(10) Patent No.: US 7,538,100 B2
(45) Date of Patent: *May 26, 2009

(54) 17α-ALKYL-17β-OXY-ESTRATRIENES AND INTERMEDIATE PRODUCTS FOR THEIR PRODUCTION, USE OF THE 17α-ALKYL-17β-OXY-ESTRATRIENES FOR THE PRODUCTION OF PHARMACEUTICAL AGENTS AS WELL AS PHARMACEUTICAL PREPARATIONS

(75) Inventors: Rolf Bohlmann, Berlin (DE); Nikolaus Heinrich, Berlin (DE); Rolf Jautelat, Berlin (DE); Jorg Kroll, Berlin (DE); Orlin Petrov, Berlin (DE); Andreas Reichel, Berlin (DE); Jens Hoffmann, Mühlenbeck (DE); Rosemarie Lichtner, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/188,992

(22) Filed: Jul. 26, 2005

(65) Prior Publication Data

US 2006/0009436 A1     Jan. 12, 2006

Related U.S. Application Data

(63) Continuation of application No. 10/305,418, filed on Nov. 27, 2002, now Pat. No. 7,018,994.

(30) Foreign Application Priority Data

Nov. 27, 2001    (DE) ................. 101 59 217

(51) Int. Cl.
*A61K 31/56*    (2006.01)
*C07J 1/00*    (2006.01)

(52) U.S. Cl. .............. 514/179; 514/182; 552/539; 552/626

(58) Field of Classification Search ........... 514/179, 514/182; 552/539, 626
See application file for complete search history.

(56) References Cited

U.S. PATENT DOCUMENTS

| 3,804,866 A | 4/1974 | Anner et al. |
|---|---|---|
| 4,775,661 A | 10/1988 | Labrie |
| 5,733,902 A | 3/1998 | Schneider et al. |
| 6,271,403 B1 | 8/2001 | Bohlmann et al. |
| 6,288,051 B1 | 9/2001 | Bittler et al. |
| 6,316,432 B1 | 11/2001 | Schwede et al. |
| 6,677,324 B1 * | 1/2004 | Knauthe et al. ............. 514/170 |
| 6,780,855 B2 | 8/2004 | Bohlmann et al. |
| 2003/0069434 A1 | 4/2003 | Bohlmann et al. |
| 2003/0191099 A1 | 10/2003 | Bohlmann et al. |
| 2005/0014736 A1 | 1/2005 | Fuhrmann et al. |
| 2007/0238714 A1 | 10/2007 | Fuhrmann et al. |

FOREIGN PATENT DOCUMENTS

| DE | 2118995 | 11/1971 |
|---|---|---|
| EP | 0 138 504 | 4/1985 |
| EP | 0138504 | 4/1985 |
| EP | 0310542 | 4/1989 |
| SU | 437 279 | 12/1974 |
| WO | WO 97/45441 | 12/1997 |
| WO | WO 98/07740 | 2/1998 |
| WO | WO 98/33855 | 8/1998 |
| WO | WO 98/34947 | 8/1998 |
| WO | WO 99/33855 | 7/1999 |
| WO | WO 9933855 | 7/1999 |
| WO | WO 99/42109 | 8/1999 |
| WO | WO 0232430 | 4/2002 |
| WO | WO 03045972 | 6/2003 |

OTHER PUBLICATIONS

English translation of International Examination Report, Mar. 2004.
Tonetti and Jordan, Journal of Mammary Gland Biology and Neoplasia, 1999; 4(4): 401-413.
Office Action of Oct. 22, 2008 - U.S. Appl. No. 10/854,761, now published - 2005/0014736 - Jan. 20, 2005.

\* cited by examiner

*Primary Examiner*—Barbara P Badio
(74) *Attorney, Agent, or Firm*—Millen, White, Zelano & Branigan, P.C.

(57) ABSTRACT

The invention relates to 17α-alkyl-17β-oxy-estra-1,3,5(10)-trienes that have an antiestrogenic action with general formula I. In addition, the invention also relates to 17-oxo-estra-1,3,5(10)-trienes as well as 17β-hydroxy-estra-1,3,5(10)-trienes as intermediate products in the production of the estratrienes according to the invention. The invention also relates to the use of 17α-alkyl-17β-oxy-estratrienes for the production of pharmaceutical agents as well as pharmaceutical preparations that contain at least one 17α-alkyl-17β-oxy-estratriene as well as at least one pharmaceutically compatible vehicle.

27 Claims, 4 Drawing Sheets

Degradation of Compound 1 and Development of Compound 3 After Incubation with Hepatic Microsomes Metabolic Stability of Compound 2 After Incubation with Hepatic and Intestinal Microsomes

17α-ALKYL-17β-OXY-ESTRATRIENES AND INTERMEDIATE PRODUCTS FOR THEIR PRODUCTION, USE OF THE 17α-ALKYL-17β-OXY-ESTRATRIENES FOR THE PRODUCTION OF PHARMACEUTICAL AGENTS AS WELL AS PHARMACEUTICAL PREPARATIONS

This application is a continuation of U.S. Ser. No. 10/305,418, filed on Nov. 27, 2002, which granted as U.S. Pat. No. 7.018,994.

The invention relates to 17α-alkyl-17β-oxy-estratrienes and intermediate products for their production, use of the 17α-alkyl-17β-oxy-estratrienes for the production of pharmaceutical agents as well as pharmaceutical preparations that contain these compounds.

The compounds according to the invention have antiestrogenic action, i.e., these substances exert inhibiting actions relative to estrogens. Such substances have already been described extensively.

For example, compounds that have an antiestrogenic action are known from EP 0 138 504 B1. These are then essentially estra-1,3,5(10)-triene derivatives, which are substituted in 3-position, i.a., with hydroxy or alkoxy, in 17β-position with hydroxy, and in 17β-position, i.a., with hydrogen or alkyl. In 7α-position, these compounds also have an alkyl side chain that can be partially fluorinated and that can be interrupted by, i.a., amido, amino, amine-N-oxide, oxy, sulfanyl, sulfinyl and/or sulfonyl groups.

In WO 99/33855 A1, 11β-halogen-7α-substituted estra-1,3,5(10)-trienes are described that can have hydroxy groups in 3-position and in 17-position. The 7α-side chain is a partially fluorinated, optionally unsaturated hydrocarbon chain that is interrupted by an amine-nitrogen atom or a sulfany, sulfinyl or sulfonyl group.

Other compounds are described in WO 98/07740 A1. In this connection, these are substituted 7α-(ξ-aminoalkyl)-estra-1,3,5(10)-trienes. These compounds preferably have a hydroxy, methoxy or acetyloxy group in 3-position and preferably a methyl or trifluoromethyl group in 17α-position and/or 17β-position. In 11β-position, a fluorine atom is preferably provided, and in 7α-position, an alkyl side chain that is at least partially fluorinated in the terminal position and that is interrupted by an amine-N atom and by a sulfanyl, sulfinyl or sulfonyl group is provided.

In WO 97/45441 A1, 7α-(5-methylaminopentyl)-estra-1,3,5(10)-trienes are disclosed that have a hydroxy group in 3-position and in 17β-position. In 17α-position, a methyl or ethinyl group can be provided. The estratriene skeleton can also be substituted in 2-position with a fluorine atom.

It has turned out that the known compounds in the application form a variety of biologically very active metabolites. The formation of these metabolites results in undesirable actions and thus in an uncontrollable spectrum of action. In particular, side effects can be adjusted or the desired primary action (antiestrogenic action) is uncontrollable by spontaneous formation of these metabolites. In addition, the compatibility of the known compounds in the case of oral administration is unsatisfactory. It has turned out in particular that the known compounds promote the build-up of alveolar macrophages.

The object of this invention is therefore to find antiestrogenic compounds whose metabolism can be controlled and that therefore form little or no biologically active metabolites. In addition, it is desired that the compatibility of the compounds that are sought is satisfactory in the case of oral administration and in the case of whose dispensing, i.a., alveolar macrophages do not build up or at least build up only to a small extent.

This object is achieved by novel 17α-alkyl-17β-oxy-estratrienes according to claim 1, also by novel 17β-oxy-estratrienes according to claim 16 as well as 17-oxo-estratrienes according to claim 18, which can be used in each case as intermediate products for the production of 17α-alky-17β-oxy-estratrienes according to the invention, also by the use of 17α-alkyl-17β-oxy-estratrienes for the production of pharmaceutical agents according to claim 20 and by the pharmaceutical compositions according to claim 21 that contain the compounds according to the invention.

The 17α-alkyl-17β-oxy-estratrienes according to the invention have general formula I:

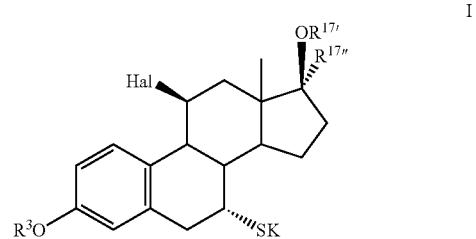

Here, in particular:

Hal means F or Cl; this radical is bonded in 11β-position to the estratriene skeleton;

$R^3$ means hydrogen, $C_1$-$C_4$-alkyl, -alkanoyl or, in more cyclic terms, $C_3$-$C_7$-ether with an O atom, $R^{17'}$ means hydrogen, $C_1$-$C_4$-alkyl and $C_1$-$C_4$-alkanoyl, $R^{17''}$ means $C_1$-$C_4$-alkyl, $C_1$-$C_4$-alkinyl as well as an at least partially fluorinated alkyl radical, whereby $R^{17'}$ means —O in 17β-position and $R^{17''}$ in 17α-position is bonded to the estratriene skeleton;

SK means -U-V-W-X-Y-Z-E, whereby this grouping is bonded via U in 7α-position to the estratriene skeleton.

In the side chain, the symbols U, V, W, X, Y, Z and E have the following meanings:

U represents either a straight-chain or branched-chain $C_1$-$C_{13}$-alkylene, -alkenylene or -alkinylene radical or the group A-B, whereby A is bonded to the estratriene skeleton and represents a benzylidene radical that is bonded via —$CH_2$— to the estratriene skeleton, a phenylene radical or a $C_1$-$C_3$-alkylaryl radical that is bonded via the alkyl group to the estratriene skeleton, and B stands for a straight-chain or branched-chain $C_1$-$C_{13}$-alkylene, -alkenylene or -alkinylene radical, and whereby A and B also can be connected to one another via an O atom.

V represents a $CH_2$ group or a C(O) group.

W is an N($R^6$) group or an $N^+(O^-)(R^6)$ group or an azolidinylene ring or an azolidinylene-N-oxide ring, whereby the azolidinylene ring or azolidinylene-N-oxide ring includes at least one C atom of grouping X, whereby $R^6$ is also either H or $CH_2$—$R^7$ or C(O)—$R^7$, in which $R^7$ can mean, as follows.

a) Hydrogen or b) A straight-chain or branched-chain, non-fluorinated or at least partially fluorinated $C_1$-$C_{14}$-alkyl, -alkenyl or -alkinyl radical, which can be hydroxylated in one or more places and which can be interrupted by one to three of the heteroatoms —O— and —S— and/or the groupings —$NR^9$—, in which $R^9$ stands for hydrogen or a $C_1$-$C_3$-alkyl radical, or c) an unsubstituted or substituted aryl or heteroaryl radical, or
d) an unsubstituted or substituted $C_3$-$C_{10}$-cycloalkyl radical, or
e) an unsubstituted or substituted $C_4$-$C_{15}$-cycloalkylalkyl radical, or
f) an unsubstituted or substituted $C_7$-$C_{20}$-aralkyl radical, or
g) an unsubstituted or substituted heteroaryl-$C_1$-$C_6$-alkyl radical or
h) an unsubstituted or substituted aminoalkyl radical or a biphenyl radical, X is preferably a straight-chain or branched-chain $C_1$-$C_{12}$-alkylene, -alkenylene or -alkinylene radical.

Y can be a direct bond between X and Z. Y can also mean the following, however:

a) an $SO_n$-$R^{10}$ group, only if W is an $N^+(O^-)(R^6)$ group or an azolidinylene-N-oxide ring and not an $N(R^6)$ group or an azolidinylene ring, whereby n=0, 1 or 2, and whereby $R^{10}$ represents a direct bond between $SO_n$ and Z or a straight-chain or branched-chain $C_1$-$C_6$-alkylene, -alkenylene or -alkinylene radical,
b) or the group $R^{11}$ or O—$R^{11}$, whereby $R^{11}$ stands for
   i) a straight-chain or branched-chain $C_1$-$C_5$-alkylene-, -alkenylene- or -alkinylene radical or for
   ii) an unsubstituted or substituted aryl radical or heteroaryl radical or for
   iii) an unsubstituted or substituted $C_3$-$C_{10}$-cycloalkyl radical or for
   iv) an unsubstituted or substituted $C_4$-$C_{15}$-cycloalkylalkyl radical or for
   v) an unsubstituted or substituted $C_7$-$C_{20}$-aralkyl radical or for
   vi) an unsubstituted or substituted heteroaryl-$C_1$-$C_6$-alkyl radical, or
c) the grouping CH=CF or
d) the grouping HN—C(O)—NH—$R^{12}$,
   whereby $R^{12}$ stands for an unsubstituted or substituted arylene radical and whereby $R^{12}$ is bonded to Z.

Z represents a direct bond between Y and E or a straight-chain or branched-chain $C_1$-$C_9$-alkylene, -alkenylene or -alkinylene radical, which can be partially or completely fluorinated.

E is a $CF_3$ group or an at least partially fluorinated aryl group, in particular a phenyl group.

Moreover, preferably hydrogen atoms are bonded to positions 1, 2, 4, 6 to 9 and 11 to 16 in the estratriene skeleton. In principle, however, the estratriene skeleton can also be modified, for example by a hydrocarbon bridge, for example a 15β,16 β-methano group.

Hal in particular stands for fluorine.

$R^3$ can be hydrogen, methyl, ethyl, n-propyl, iso-propyl, n-butyl, iso-butyl and tert-butyl, a corresponding alkanoyl (acetyl, propionyl, butanoyl) or a cyclic ether. $R^3$ in particular stands for hydrogen, $CH_3$, $CH_3CO$ or $C_5H_{10}O$.

$R^{17'}$ and $R^{17''}$ are in particular methyl, ethyl, n-propyl, iso-propyl, n-butyl, iso-butyl and tert-butyl, whereby $R^{17'}$ in addition can also be hydrogen, acetyl, propionyl and butanoyl, and whereby in this case, the corresponding isomers can be included. In addition. $R^{17''}$ can be ethinyl, 1-propinyl, 2-propinyl, 1-butinyl, 2-butinyl and 3-butinyl as well as trifluoromethyl, pentafluoroethyl, heptafluoropropyl and nonafluorobutyl, whereby in this case, the corresponding isomers are also included. $R^{17'}$ is in particular hydrogen, $CH_3$ or $CH_3CO$. $R^{17''}$ preferably stands for methyl, ethinyl and trifluoromethyl.

U can be in particular a straight-chain or branched-chain alkylene radical and in particular a methylene, ethylene, propylene, butylene, pentylene, hexylene, heptylene, octylene, nonylene, decylene, undecylene, dodecylene or tridecylene radical. U preferably stands for $(CH_2)_p$, whereby p is an integer from 2 to 10. In particular, U is preferably a butylene, pentylene, hexylene or heptylene radical. U is quite especially preferably an n-butylene radical, i.e., in the formula $(CH_2)_p$ for U, p=4.

In particular, V stands for $CH_2$. The grouping U-V thus can be n-pentylene in a quite preferred embodiment.

In particular, W stands for the amine-N-oxide $N^+(O^-)(R^6)$ or for the amine $N(R^6)$, whereby $R^6$ is preferably hydrogen or $CH_2$—$R^7$, in which $R^7$ stands in particular for hydrogen or methyl or ethyl. $R^6$ is thus preferably hydrogen or a $C_1$-$C_3$-alkyl radical, thus in particular a methyl, ethyl, n-propyl or iso-propyl radical. In an especially preferred embodiment, W represents an $N^+(O^-)(CH_3)$ group (N-methylamine-N-oxide).

X preferably stands for $(CH_2)_q$, whereby q=0 or an integer from 1 to 12, thus for a direct bond between W and Y or for a straight-chain or branched methylene, ethylene, propylene, butylene, pentylene, hexylene, heptylene, octylene, nonylene, decylene, undecylene or dodecylene radical. In an especially preferred embodiment, X is an ethylene, n-propylene, n-butylene, n-pentylene, n-hexylene, n-heptylene or n-octylene radical.

In particular, Y can represent a direct bond between X and Z. If this is the case, X stands for a longer alkylene chain, thus in particular, X stands for n-hexylene, n-heptylene or n-octylene. In a preferred embodiment, Y can also be an $SO_n$ group, whereby n=0, 1 or 2, thus a sulfanyl group, a sulfinyl group or a sulfonyl group. If Y is an $SO_n$ group, X represents a rather shorter alkylene chain, in particular an n-propyl chain.

Z is preferably a direct bond between Y and E or a straight-chain or branched-chain $C_1$-$C_7$-alkylene radical, which can be at least partially fluorinated. In particular, Z can be a methylene, ethylene, propylene or butylene radical, which can be at least partially fluorinated. In particular, Z is difluoromethylene or a straight-chain alkylene radical, which is perfluorinated on one end, thus, for example, a 1,1-difluoroethylene, 1,1,2,2-tetrafluoro-n-propylene or 1,1,2,2,3-,3-hexafluoro-n-butylene radical. Alkylene radicals that carry only two fluorine atoms on a terminal C-atom are especially advantageous, whereby this $C_2F_5$ group is bonded to radical E. In this case, side chain SK is terminated with $C_2F_5$.

In particular, E stands for CF, or for pentafluorophenyl. The grouping Z-E thus preferably represents one of the groups that is selected from the group that comprises $C_2F_5$, $C_3F_7$ and $C_4F_9$ as well as $C_6F_5$.

According to this invention, pharmacologically compatible acid addition salts as well as esters of 17α-alkyl-17β-oxy-estratrienes are also included. The addition salts are the corresponding salts with inorganic and organic acids. As addition salts, in particular the hydrochlorides, hydrobromides, acetates, citrates, oxalates, tartrates and methanesulfonates are considered. If $R^3$ and $R^{17}$ are hydrogen, such that a 3,17β-diol is present, the esters of these hydroxy compounds can also be formed. These esters are preferably formed with organic acids, whereby the same acids as for forming the addition salts are suitable, namely in particular acetic acid, but also higher carboxylic acids, such as, e.g., propionic, butyric, isobutyric, valeric, isovaleric or pivalic acid.

The novel 17α-alkyl-17β-oxy-estratrienes have several chiral centers, for example also on an N atom that is optionally oxidized to form N-oxide. There are therefore several stereoisomeric forms of each compound in each case. The compounds of formula I can be present as tautomers, stereoisomers or geometric isomers. The invention also comprises all possible isomers such as E- and Z-isomers, S- and R-enantiomers, diastereomers, racemates and mixtures thereof including the tautomeric compounds. All of these isomeric compounds are—even if not expressly indicated in each case—components of this invention. The isomeric mixtures can be separated into enantiomers or E/Z-isomers according to commonly used methods, such as, for example, crystallization, chromatography or salt formation.

Especially suitable compounds as defined by the invention are estratrienes with general formula I, namely
1) 11β-Fluoro-7α-{5-[methyl(7,7,8,8,9,9,9-heptafluorononyl)amino]pentyl}-17α-methylestra-1,3,5(10)-triene-3,17β-diol N-oxide
2) 11β-Fluoro-7α-{5-[methyl(8,8,9,9,10,10,10-heptafluorodecyl)amino]pentyl}-17α-methylestra-1,3,5(10)-triene-3,17β-diol N-oxide
3) (RS)-11β-Fluoro-7α-{5-[methyl(7,7,8,8,9,9,10,10,10-nonafluorodecyl)amino]-pentyl}-17α-methylestra-1,3,5(10)-triene-3,17β-diol N-oxide
4) 11β-Fluoro-7α-{5-[methyl(8,8,9,9,9-pentafluorononyl)amino]pentyl}-17α-methylestra-1,3,5(10)-triene-3,17β-diol N-oxide
5) 11β-Fluoro-7α-{5-[methyl(9,9,10,10,10-pentafluorodecyl)amino]pentyl-17α-methylestra-1,3,5(10)-triene-3,17-diol N-oxide
6) 11β-Fluoro-7α-{5-[methyl(8,8,9,9,9-pentafluorononyl)amino]pentyl}-17α-methylestra-1,3,5(10)-triene-3,17β-diol
7) 11β-Fluoro-7α-{5-[methyl(7,7,8,8,9,9,10,10,10-nonafluorodecyl)amino]pentyl}-17α-methylestra-1,3,5(10)-triene-3,17β-diol
8) 11β-Fluoro-7α-{5-[methyl(7,7,8,8,9,9,9-heptafluorononyl)amino]pentyl}-17α-methylestra-1,3,5(10)-triene-3,17β-diol
9) 17β-Ethinyl-11β-fluoro-7α-{5-[methyl(7,7,8,8,9,9,10,10,10-nonafluorodecyl)-amino]pentyl}-estra-1,3,5(10)-triene-3,17β-diol
10) 17β-Ethinyl-11β-fluoro-3-(2-tetrahydropyranoyloxy)-7α-{5-[methyl(7,7,8,8,9,9,10,10,10-nonafluorodecyl)amino]pentyl}-estra-1,3,5(10)-trien-17β-ol
11) 11β-Fluoro-3-(2-tetrahydropyranyloxy)-7α-{5-[methyl(7,7,8,8,9,9,10,10,10-nonafluorodecyl)amino]pentyl}-17α-methylestra-1,3,5(10)-trien-17β-ol
12) 11β-Fluoro-7α-{5-[methyl(7,7,8,8,9,9,10,10,10-nonafluorodecyl)amino]pentyl}-17α-trifluoromethylestra-1,3,5(10)-triene-3,17β-diol
13) 11β-Fluoro-7α-{5-[methyl(6,6,7,7,8,8,8-heptafluorooctyl)amino]pentyl}-17α-methylestra-1,3,5(10)-triene-3,17β-diol
14) 11β-Fluoro-7α-{5-[methyl(8,8,9,9,10,10,10-heptafluorodecyl)amino]pentyl}-17α-methylestra-1,3,5(10)-triene-3,17β-diol
15) 11β-Fluoro-7α-{5-[methyl(6,6,7,7,8,8,9,9,10,10,10-undecafluorodecyl)amino]-pentyl}-17α-methylestra-1,3,5(10)-triene-3,17β-diol
16) 11β-Fluoro-7α-{5-[methyl(5,5,6,6,7,7,8,8,8-nonafluorooctyl)amino]pentyl}-17α-methylestra-1,3,5(10)-triene-3,17β-diol
17) 11β-Fluoro-7α-{5-[methyl(9,9,10,10,11,11,11-heptafluoroundecyl)amino]-pentyl}-17α-methylestra-1,3,5(10)-triene-3,17β-diol
18) 11β-Fluoro-7α-{-[methyl(9,9,10,10,10-pentafluorodecyl)amino]pentyl}-17α-methylestra-1,3,5(10)-triene-3,17β-diol Physical properties of some of these compounds are indicated in Table 1.

The 17α-alkyl-17β-oxy-estratrienes according to the invention are distinguished from known compounds primarily in that a halogen atom is bonded in 11α-position, and/or an alkyl radical is bonded in 17α-position. In addition, preferred compounds in the 7α-side chain can have an amine-N-oxide grouping.

In contrast to 3,17β-dihydroxy-estratrienes, which are unsubstituted in 17α-position, virtually no metabolites are formed from the 17α-alkyl-17β-oxy-estratrienes according to the invention. Metabolites can also be biologically active. It has namely been revealed that the estratrienes that are produced by oxidation of the hydroxy group that is bonded in 17β-position, whereby a 17-oxo derivative is produced, have very strong biological activity.

By blocking the 17α position by an alkyl radical, especially by a $C_1$-$C_4$-alkyl group, this oxidation reaction is stopped, such that a metabolic variety is also suppressed. The estratrienes according to the invention that are used as active ingredients therefore exhibit a species-independent effectiveness and activity. The advantage of these compounds therefore exists in that the full effectiveness of the active ingredient is achieved in a single compound.

For this reason, advantages arise in the development of pharmaceutical agents, since owing to a lack of formation of biologically active metabolites, the effectiveness can more simply be ascribed to certain structural principles, such that a targeted search for active ingredients is made possible.

In addition, the 17α-alkyl-17β-oxy-estratrenes according to the invention inhibit the action of estradiol to approximately 100%. They therefore represent antiestrogens.

To study the effectiveness of the compounds according to the invention, in-vivo tests were performed on infant rats. To this end, the uterus growth was performed with personal (p.o.) administration of the pharmaceutical agent (test on antiestrogenic action).

The principle of this method consists in examining what influence the administration of compounds that have an antiestrogenic action has in the simultaneous administration of estrogens. In the case of rodents, the uterus reacts to the dispensing of estrogens namely with a weight increase (both by proliferation and by water retention). This growth can be inhibited in a dose-dependent manner by simultaneous administration of compounds that have an antiestrogenic action.

For the tests, infant female rats with a weight of 35-45 g at the beginning of the test were studied. Five to six animals were tested per dose. For the p.o. administration, the substances were dissolved in one portion of ethanol (E) and were filled out with nine portions of peanut oil (EÖ). For acclimation, the young rats just dropped by the mothers were delivered one day before the beginning of treatment and immediately supplied with food—right in the cage. The animals were then treated—in combination with 0.5 µg of estradiolbenzoate (EB) once daily for three days. EB was always administered subcutaneously (s.c.), while the test substance was administered p.o. 24 hours after the last administration, the animals were weighed, killed, and the uteri were removed. The moist weights (less contents) were determined from the prepared uteri. The following control studies were performed: for a negative control, 0.2 ml of an E/EÖ mixture per animal and day was added. For a positive control study, 0.5 µg of EB/0, 1 ml per animal and day, was administered.

From the relative organ weights (mg/110 g of body weight), the average values with standard deviation (X±SD) as well as the significance of the differences in the control group (EB) in the Dunnett Test (p<0.05) were determined for each group. The inhibition (in %) relative to the EB control was determined with a computer program. The relative effectiveness of the test substances was calculated by a covariance and regression analysis.

Test results for selected compounds are reproduced in Table 2. Test results for the uterus growth with simultaneous administration of 0.5 µg of EB/O, 1 ml s.c., as well as peroral dispensing of the compounds that have an antiestrogenic action in an amount in the range of 0.03 mg/kg of body weight and 0.3 mg/kg of body weight are reproduced there.

It can be seen from Table 2 that the antiestrogenic action is nearly 100% when a dosage of about 0.3 mg/kg in the case of peroral administration was added.

The compounds according to the invention are as effective as or even more effective than the corresponding compounds that are not substituted in 17β-position. Compared to the compounds that are not substituted in 17α-position, the estratrienes according to the invention in addition have a better compatibility, such that the latter are to be preferred. The better compatibility can be attributed in particular to the fact that the formation of metabolites is largely limited.

Determination of metabolic stability: in-vitro 17β-HSD test

17β-HSD2 mediates the intestinal enzymatic dehydrogenization of an OH group in 17-position of the sterane skeleton into a ketone group.

For this test, the following materials are used:
Na-Phosphate buffer: 100 mmol of $Na_2HPO_4 \times 2H_2O$ and 100 mmol of $NaH_2PO_4 \times H_2O$
Test substance solution of
11β-Fluoro-7α-{5-[methyl(8,8,9,9,9-pentafluorononyl)amino]pentyl}-17α-methylestra-1,3,5(10)-triene-3,17β-diol (compound 1, as a representative of the compounds of general formula I) and
11β-Fluoro-7α-{5-[methyl(8,8,9,9,9-pentafluorononyl)amino]pentyl-estra-1,3,5(10)-triene-3,17β-diol (compound 2): 15 µmol in MeOH (0.3 mmol in the test batch).
Cofactor solution: 2 ml of glucose-6-phosphate (160 mmol)/$MgCl_2$ (80 mmol) mixture is added to 400 µl of a glucose-6-phosphate-dehydrogenase solution, and then 15.6 mg of NADP and 13.4 mg of NAD are added.
Microsome solution: intestinal microsomes (InVitroTechnologies; protein content: 24 mg/ml; CYP450 content: 0.058 nmol/mg of protein)
In the water bath, it is thawed at 37° C. (60 seconds) and diluted with Na-phosphate buffer to a concentration of 5 mg/ml of protein.
In each case, 170 µl/well of the buffer and 5 µl/well of the test substance solutions are introduced into the corresponding wells, whereby double values are applied for each measuring time (0, 10, 20, 30, 45 and 60 minutes).
In each case, 250 µl of ice-cold MeOH is added to the 0-minute values. Then, 25 µl of microsome solution and 50 µl of cofactor solution are added immediately to all wells. The samples of the 0-minute values are stored without incubation at ~−20° C. for about 24 hours. The other samples are incubated in each case for 10, 20, 30, 45 and 60 minutes at 37° C., and the dehydrogenation reaction is stopped after these times by the addition of 250 µl of ice-cold MeOH in each case. The samples are stored until measurement per LC/MS/MS at ~−20° C. for about 24 hours and centrifuged at 3000 rpm before analysis, whereby the supernatant is measured.

The concentrations of the test substances measured per LC/MS/MS and the resulting 17 ketone product are reproduced in FIGS. 2a-2f.

Compound 1 is metabolically stable in intestinal microsomes but not in liver microsomes, which indicates that different phase-1 reactions occur in both tissues. The putative product of the 17βSD-reaction, 11β-fluoro-7α-{5-[methyl(8,8,9,9,9-pentafluorononyl)amino]pentyl}-estra-1,3,5(10)-trien-3-ol-17-one, compound 3, does not occur in any of the tissues, however. In contrast to this, compound 2, which does not have any 17 methyl group, is degraded in intestinal microsomes, whereby the corresponding 17-ketone is produced.

Consequently, the high metabolic stability of compound 1 can be explained by the blocking of the 17βHSD reaction, which is completely stopped by a 17β-methyl group. It therefore has to be assumed from this that an alkyl group, for example a methyl group, or else an alkenyl or alkinyl group, for example an ethinyl group, in the vicinity of the 17-OH group, prevents the intestinal (in contrast to the hepatic) oxidation thereof to ketone, surprisingly enough, which should have the result of higher oral bioavailability.

In addition, the compounds according to the invention are thus distinguished by an extraordinarily high bioavailability, such that high serum levels can be reached by the administration of the compounds according to the invention to the affected patients. In connection with the already mentioned high compatibility, a successful and reliable therapy can thus be performed since it is possible with the compounds according to the invention to set a serum level of the active compound that has a sufficient distance to the effect level of the corresponding compound. Effect level means the serum concentration of the active ingredient that is necessary at the least to achieve the desired effect in the respective indication.

The 17α-alkyl-17β-oxy-estratrienes with general formula 1 according to the invention are suitable in particular for the production of pharmaceutical agents. The invention therefore relates in addition to the pharmaceutical preparation that in addition to at least one 17α-alkyl-17β-oxy-estratriene with general formula I, which has the substituents Hal, $R^3$, $R^{17'}$, $R^{17''}$, U, V, W, X, Y, Z and E according to the definitions above, contains at least one pharmaceutically compatible vehicle.

The pharmaceutical preparations or compositions according to the invention are produced with commonly used solid or liquid vehicles or diluents and commonly used pharmaceutical and technical adjuvants according to the desired type of administration with a suitable dosage in a way that is known in the art. Preferred preparations consist of a dispensing form that is suitable for oral, enteral, or parenteral administration, for example i.p. (intraperitoneal), i.v. (intravenous), i.m. (intramuscular) or percutaneous, administration. Such dispensing forms are, for example, tablets, film tablets, coated tablets, pills, capsules, powders, creams, ointments, lotions, liquids, such as syrups, gels, injectable liquids, for example for i.p., i.v., i.m. or percutaneous injection, etc. In addition, depot forms, such as implantable preparations, as well as suppositories, are also suitable. In this case, depending on their type, the individual preparations release to the body the estratrienes according to the invention gradually or all at once in a short time.

For oral administration, capsules, pills, tablets, coated tablets and liquids or other known oral forms for dispensing can be used as pharmaceutical preparations. In this case, the pharmaceutical agents can be formulated in the way that they release the active ingredients either in a short time and pass on to the body or have a depot action; so that a longer-lasting, slow supply of active ingredients to the body is achieved. In addition to at least one estratriene, the dosage units can contain one or more pharmaceutically compatible vehicles, for example substances for adjusting the rheology of the pharmaceutical agent, surfactants, solubilizers, microcapsules, microparticles, granulates, diluents, binders, such as starches, sugar, sorbitol and gelatins, also fillers, such as silicic acid and talc, lubricants, dyes, perfumes and other substances.

Corresponding tablets can be obtained, for example, by mixing active ingredient with known adjuvants, for example inert diluents such as dextrose, sugar, sorbitol, mannitol, polyvinyl pyrrolidone, explosives such as corn starch or alginic acid, binders such as starch or gelatin, lubricants such as carboxypolymethylene, carboxy methyl cellulose, cellulose acetate phthalate or polyvinyl acetate. The tablets can also consist of several layers.

Coated tablets can be produced accordingly by coating cores that are produced analogously to the tablets with agents that are commonly used in coated tablet coatings, for example polyvinylpyrrolidone or shellac, gum arabic, talc, titanium oxide or sugar. In this case, the shell of the coated tablet can also consist of several layers, whereby the adjuvants that are mentioned above in the case of the tablets can be used.

Capsules that contain active ingredients can be produced, for example, by the active ingredient being mixed with an inert vehicle such as lactose or sorbitol and encapsulated in gelatin capsules.

The estratrienes according to the invention can also be formulated in the form of a solution that is intended for oral administration and that in addition to the active estratriene contains as components a pharmaceutically compatible oil and/or a pharmaceutically compatible lipophilic surfactant and/or a pharmaceutically compatible hydrophilic surfactant and/or a pharmaceutically compatible water-miscible solvent.

To achieve better bio-availability of the active ingredients according to the invention, the compounds can also be formulated as cyclodextrin clathrates. To this end, the compounds are reacted with $\alpha$-, $\beta$- or $\gamma$-cyclodextrin or derivatives thereof.

If creams, ointments, lotions and liquids that can be applied topically are to be used, the latter must be constituted so that the compounds according to the invention are fed to the body in adequate amounts. In these forms for dispensing, adjuvants are contained, for example substances for adjusting the rheology of pharmaceutical agents, surfactants, preservatives, solubilizers, diluents, substances for increasing the permeability of the estratrienes according to the invention through the skin, dyes, perfumes and skin protection agents, such as conditioners and moisturizers. Together with the compounds according to the invention, other active ingredients can also be contained in the pharmaceutical agent [*Üllmanns Enzyklopädie der technischen Chemie [Ullmann's Encyclopedia of Technical Chemistry], Volume* 4 (1953), pages 1-39; *J. Pharm. Sci.,* 52, 918 ff. (1963); issued by Czetsch-Lindenwald, Hilfsstoffe für Pharmazie und angrenzende Gebiete [Adjuvants for Pharmaceutics and Related Fields], Pharm. Ind., 2, 72 ff (1961); Dr. H. P. Fiedler, *Lexikon der Hilfstooffe für Pharmazie, Kosmetik und angrenzende Gebiete [Dictionary of Adjuvants for Pharmaceutics, Cosmetics and Related Fields]*, Cantor A G, Aulendorf/Württ., 1971].

The substances according to the invention can also be used in suitable solutions, such as, for example, physiological common salt solution, as infusion or injection solutions. For parenteral administration, the active ingredients can be dissolved or suspended in a physiologically compatible diluent. As diluents, in particular oily solutions, such as for example solutions in sesame oil, castor oil and cottonseed oil, are suitable. To increase solubility, solubilizers, such as, for example, benzyl benzoate or benzyl alcohol, can be added.

To formulate an injectable preparation, any liquid vehicle can be used in which the compounds according to the invention are dissolved or emulsified. These liquids frequently also contain substances to regulate viscosity, surfactants, preservatives, solubilizers, diluents and other additives, with which the solution is set to isotonic. Other active ingredients can also be administered together with the estratrienes.

The estratrienes according to the invention can also be applied in the form of a depot injection or an implant preparation, for example subcutaneously. Such preparations can be formulated in such a way that a delayed release of active ingredients is made possible. To this end, known techniques can be used, for example depots that dissolve or operate with a membrane. Implants can contain as inert materials, for example, biodegradable polymers or synthetic silicones, for example silicone gum. The estratrienes can also be incorporated in, for example, a patch, for percutaneous administration.

It is also possible to incorporate the substances according to the invention in a transdermal system and thus to administer them transdermally.

To achieve an improved transdermal skin flow that produces therapeutically effective blood levels, the compounds according to the invention can also be incorporated in transdermal systems analogously to what is described for other antiestrogens in WO 01/76608. These transdermal systems are distinguished by a special ratio of 2 penetration intensifiers, in particular lauric acid and propylene glycol.

The dosage of the substances of general formula I according to the invention is determined by the attending physician and depends on, i.a., the substance that is administered, the method of administration, the disease that is to be treated and the severity of the disease. The amount of the compounds to be administered fluctuates within a wide range and can cover any effective amount. Based on the condition to be treated and on the type of administration, the amount of administered compound can be 0.1-25 mg/kg of body weight, preferably 0.5-5 mg/kg of body weight, per day. In humans, this corresponds to a daily dose of 5-1250 mg. The preferred daily dosage in humans is 50-200 mg. This applies in particular to tumor therapy. The dose can be given as a single dose to be administered once or divided into two or more daily doses.

The compounds of general formula I represent, as already mentioned, compounds with very strong antiestrogenic action.

The compounds are suitable for therapy of estrogen-dependent diseases, for example, breast cancer (second-line therapy of tamoxifen-resistant breast cancer; for adjuvant treatment of breast cancer instead of tamoxifen), endometrial carcinoma, prostate hyperplasia, anovulatory infertility and melanoma.

The compounds of general formula I can also be used as components in the products that are described in, i.a., EP 346 014 B1, whereby said products contain an estrogen and a pure antiestrogen, namely for simultaneous, sequential or separate use for the selective estrogen therapy of perimenopausal or postmenopausal women.

The compounds of general formula I can be used together with antigestagens (competitive progesterone antagonists) to treat hormone-dependent tumors (EP 310 542 A).

Other indications in which the compounds of general formula I can be used is male hair loss, diffuse alopecia, an alopecia caused by chemotherapy as well as hirsutism (Hye-Sun Oh, and Robert C. Smart, Proc. Natl. Acad. Sci. USA (93/1996) 12525-12530).

In addition, the compounds of general formula I can be used for the production of medications for treating endometriosis.

The compounds of general formula I can also be used for the production of pharmaceutical compositions for male and female birth control (male birth control: DE 195 10 862.0 A).

The estratrienes according to the invention can be produced analogously to the known process:

In FIG. 1, a reaction diagram is reproduced, according to which the compounds according to the invention can be produced. In this diagram, the 17α-alkyl-17β-oxy-estratrienes according to the invention are referred to with the term "17β-methyl-amine" and "17α-methyl-amine-oxide." However, the compounds with the designation "17β-methyl" in 7α-position have a side chain without an amine grouping. The compounds that carry a hydroxy or alkoxy group in 17β-position, an alkyl group in 17α-position as well as a 7α-side chain with an amine grouping are referred to as "17α-methyl-amine". In a corresponding way, the compounds that are referred to as "17α-methyl-amine-oxide" are the amine-N-oxides according to the invention of the previously referenced "17α-methyl-amine" compounds.

If $R^3 \neq H$, an etherification is performed with a reagent $R^3$, in which X means a leaving group.

Compounds that are referred to as "17β-OH" are also estratrienes that have a hydroxy group or alkoxy group in 17β-position but have neither a 17α-alkyl grouping nor an amine grouping in the side chain in 7α-position. Compounds that are referred to as "17-keto" are estratrienes that carry an oxo group in 17-position but do not carry any amine grouping in the side chain in 7α-position. The other compounds that are referred to as "17β-OH-amine," "17-keto-amine," "17 β-OH-amine-oxide" and "17-keto-amine-oxide" have corresponding substitution patterns.

In principle, all cited compounds, starting from the 17-oxo compound, can be produced. The production of the 17-oxo compounds is described by way of example in, for example, WO 99/33855 A1. Derivatives other than the compounds that are disclosed expressly in this document with the same substitution pattern can be produced analogously. In the same way, the estratrienes according to the invention can also be produced starting from the 17β-hydroxy compounds or the 17β-alkoxy compounds ("17β-OH"). The production of these derivatives is also indicated in, for example, WO 99/33855 A1. In the same way, the production of the 17β-hydroxy compounds or 17β-alkoxy compounds as well as the 17-oxo compounds with an amine grouping in the side chain in 7α-position is disclosed in this document. If the production of the starting compounds is not described, the starting compounds are known and commercially available, or the compounds are synthesized analogously to the described processes. The production of a few precursors, intermediate products and products is described by way of example.

In the production of the substances according to the invention, for example, the following processes are employed (see also, in this respect, EP 0138 504 B1; WO 97/45441 A1; WO 98/07740 A1; WO 99/33855 A1):

The 17α-alkyl-17β-oxy-estratrienes according to the invention can be produced starting from the corresponding 17β-oxy-estratrienes ("17β-OH"). The synthesis of these starting substances is also described in, for example, WO 97/45441 A1 and WO 98/07740 A1. The side chain in 7α-position can be built up, for example, according to the procedure that is indicated in WO 98/07740 A1.

Then, the 17β-hydroxy compound or the 17β-alkoxy compound that is produced can be oxidized with an amine grouping in the side chain in 7α-position by oxidation to form the corresponding 17-oxo compound ("17-keto-amine"). To this end, commonly used oxidizing agents, for example chromium(VI) compounds (Jones oxidation), nitric acid, manganese dioxide, selenium dioxide and $SO_3$ in pyridine can be used. The ketones can also be produced by catalytic dehydrogenation with metallic copper, silver, copper chromate and zinc oxide at elevated temperature or by dehydrogenation with ketones, for example cyclohexanone, by Oppenauer oxidation. If the group reducing the side chain contains, for example, S or SO groups, the latter can optionally be selectively reduced again after an over-oxidation.

In another process variant, the 17β-oxy-estratrienes without amine-purging in the 7α-side chain can be oxidized directly to the 17-oxo-estratrienes ("17-keto"), and the latter are then aminated in a known way in the 7α-side chain.

Then, an alkyl group can be introduced in 17α-position. To this end, commonly used nucleophilic alkylating reagents can be used, for example Grignard reagents or alkyllithium compounds. In this reaction, the desired 17α-alkyl-17β-oxy-estratrienes are produced ("17α-methyl," if a start is made from the corresponding 17β-hydroxy-estratrienes without an amine grouping in the side chain in 7α-position ["17β-OH"], or "17α-methyl-amine," if a start is made from the corresponding 7-hydroxy-estratrienes with an amine grouping in the side chain in 17α-position ["17β-OH-amine"]). In addition, the 17-oxo-estratrienes that are obtained as intermediate products can first be alkylated in a known way and then aminated in the 7α-side chain.

If the amine-N-oxide compounds ("17β-OH-amine-oxide" or "17-keto-amine-oxide" or "17β-methyl-amine-oxide") are to be produced, the corresponding estratrienes are oxidized with an amine grouping in the 7α-side chain ("17β-OH-amine" or "17-keto-amine" or "17α-methyl-amine"), for example with hydrogen peroxide. In this reaction, the secondary OH group in 17β-position is not oxidized.

In an alternative procedure for the production of the 17α-alkyl-17β-oxy-estratrienes according to the invention, the previously-mentioned 17β-hydroxy-estratrienes with an amine grouping in the side chain in 7α-position ("17β-OH-amine") are also used as starting substances.

The latter are first reacted to form the corresponding amine-N-oxide compounds ("17β-OH-amine-oxide"), whereby, as indicated above, commonly used oxidizing agents, for example, hydrogen peroxide, are used.

Then, the formed amine-N-oxide compounds ("17β-OH-amine-oxide") can be oxidized to the corresponding ketone ("17-keto-amine-oxide"), whereby the same oxidizing agents, as indicated above, can be used. In this case, the 17-oxo compounds with an amine-N-oxide grouping in the 7α-side chain are produced.

For the production of the 17α-alkyl-17β-oxy-estratrienes according to the invention, the keto group is in turn reacted according to the instructions above with suitable nucleophilic alkylating reagents. In this case, the 17α-alkyl-17β-oxy-estratrienes with an amine-N-oxide grouping in the 7α-side chain ("17β-methyl-amine-oxide") are produced.

For the production of the 17α-alkyl-17β-oxy-estratrienes according to the invention, i.a., intermediate products with the following general formula II are thus also formed, which also are the subjects of this invention:

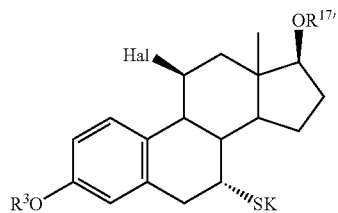
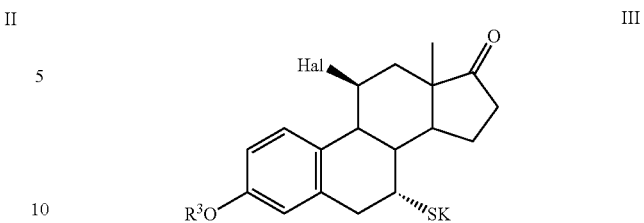

Here, in turn:

Hal =F or Cl, whereby this radical in 11β-position is bonded to the estratriene skeleton, $R^3$=hydrogen, $C_1$-$C_4$-alkyl, $C_1$-$C_4$-alkanoyl or, in more cyclic terms, a $C_3$-$C_7$-ether with an O Atom, $R^{17'}$=hydrogen, $C_1$-$C_4$-alkyl and $C_1$-$C_4$-alkanoyl, whereby $R^{17'}$ in 17β-position is bonded to the estratriene skeleton, and SK=U-V-W-X-Y-Z-E, whereby this grouping is bonded to the estratriene skeleton via U in 7α-position, and whereby U, V, X, Y, Z and E have the meanings that are further indicated above, and W stands for $N^+(O^-)(R^6)$— or for an azolidinylene-N-oxide ring, whereby the azolidinylene-N-oxide ring includes at least one C atom of grouping X, whereby $R^6$ otherwise has the meaning that is further indicated above.

In positions 1, 2, 4, 6 to 9 and 11 to 16 on the estratriene skeleton, hydrogen atoms are preferably bonded in turn, moreover. In principle, the estratriene skeleton can also be modified, however, e.g., by one hydrocarbon bridge, for example by a 15β, 16β-methano group.

Especially preferred 17α-alkyl-17β-oxy-estratrienes with an amine-N-oxide grouping in the 7α-side chain with general formula II are the following compounds:

X1) 11β-Fluoro-7α-{5-[methyl(8,8,9,9,9-pentafluorononyl)amino]pentyl} estra-1,3,5(10)-triene-3,17β-diol N-oxide X2) 11β-Fluoro-7α-[5-(methyl {3-[(2,3,4,5,6-pentafluorophenyl)sulfanyl]propyl}-amino) pentyl]estra-1,3,5(10)-triene-3,17β-diol N-oxide X3) 11β-Fluoro-7α-[5-(methyl {3-[(4,4,5,5,5-pentafluoropentyl)sulfany]-propyl}amino)pentyl]estra-1,3,5(10)-triene-3,17β-diol N-oxide X4) 11β-Fluoro-7α-[5-(methyl{3-[(4,4,5,5,5-pentafluoropentyl)sulfinyl]-propyl}amino)pentyl]estra-1,3,5 (10)-triene-3,17β-diol N-oxide X5) 11β-Fluoro-7α-{5-[methyl(7,7,8,8,9,9,10,10,10-nonafluorodecyl) amino]pentyl} estra-1,3,5(10)-triene-3,17β-diol N-oxide X6) (S)-11β-Fluoro-7α-{5-[methyl(7,7,8,8,9,9,10,10,10-nonafluorodecyl)amino]pentyl}-17α-methylestra-1,3,5 (10)-triene-3,17β-diol N-oxide X7) (R)-11β-Fluoro-7α-{5-[methyl(7,7,8,8,9,9,10,10,10-nonafluorodecyl)amino]pentyl}-17α-methylestra-1,3,5 (10)-triene-3,17β-diol N-oxide X8) 11β-Fluoro-7α-{5-[methyl(9,9,10,10,10-pentafluorodecyl)amino]pentyl} estra-1,3,5(10)-triene-3,17β-diol N-oxide.

Physical properties of these compounds are indicated in Table 3.

In addition, the 17-oxo-estratrienes with an amine-N-oxide grouping that are formed in the production of the 17α-alkyl-17β-oxy-estratrienes according to the invention in the 7α-side chain as intermediate products are also subjects of this invention. These compounds have general formula III:

Here:

Hal means F or Cl, whereby this radical is bonded in 11β-position to the estratriene skeleton, $R^3$ means hydrogen, $C_1$-$C_4$-alkyl, $C_1$-$C_4$-alkanoyl or, in more cyclic terms, a $C_3$-$C_7$-ether with an O atom, and SK means U-V-W-X-Y-Z-E, whereby this grouping is bonded via U in 7α-position to the estratriene skeleton and whereby U, V, X, Y, Z and E have the meanings that are further indicated above, and WV stands for an $N^+(O^-)(R^6)$ group or for an azolidinylene-N-oxide ring, whereby the azolidinylene-N-oxide ring includes at least one C atom of grouping X, whereby $R^6$ also has the meaning that is further indicated above.

In positions 1, 2, 4, 6 to 9 and 11 to 16 on the estratriene skeleton, moreover, preferably hydrogen atoms are bonded in turn. In principle, the estratriene skeleton can also be modified, but, e.g., by a hydrocarbon bridge, for example a 15β, 16β-methano group.

Especially preferred 17-oxo-estratrienes with an amine-N-oxide grouping in the 7α-side chain with general formula III are the following compounds:

Y1 11β-Fluoro-7α-[5-(methyl {3-[(4,4,5,5,5-pentafluoropentyl)sulfinyl]propyl}-amino)pentyl]estra-1,3,5(10)-trien-3-ol-17-one N-oxide Y2 11β-Fluoro-7α-[5-(methyl {3-[(4,4,5,5,5-pentafluoropentyl)sulfanyl]propyl}-amino)pentyl]estra-1,3,5(10)-trien-3-ol-17-one N-oxide Y3 11β-Fluoro-7α-{5-[methyl(7,7,8,8,9,9,10,10,10-nonafluorodecyl)amino]pentyl}-estra-3,5(10)-trien-3-ol-17-one N-oxide.

Physical properties of these compounds are indicated in Table 4.

The compounds of general formula II and the compounds of general formula III are also compounds with antiestrogenic action. They can therefore be used in principle in the types of indications indicated above for the compounds of general formula I.

Below, the process steps for the production of the compounds according to the invention are described in more detail.

BRIEF DESCIPTION OF DRAWINGS

Figure 1:
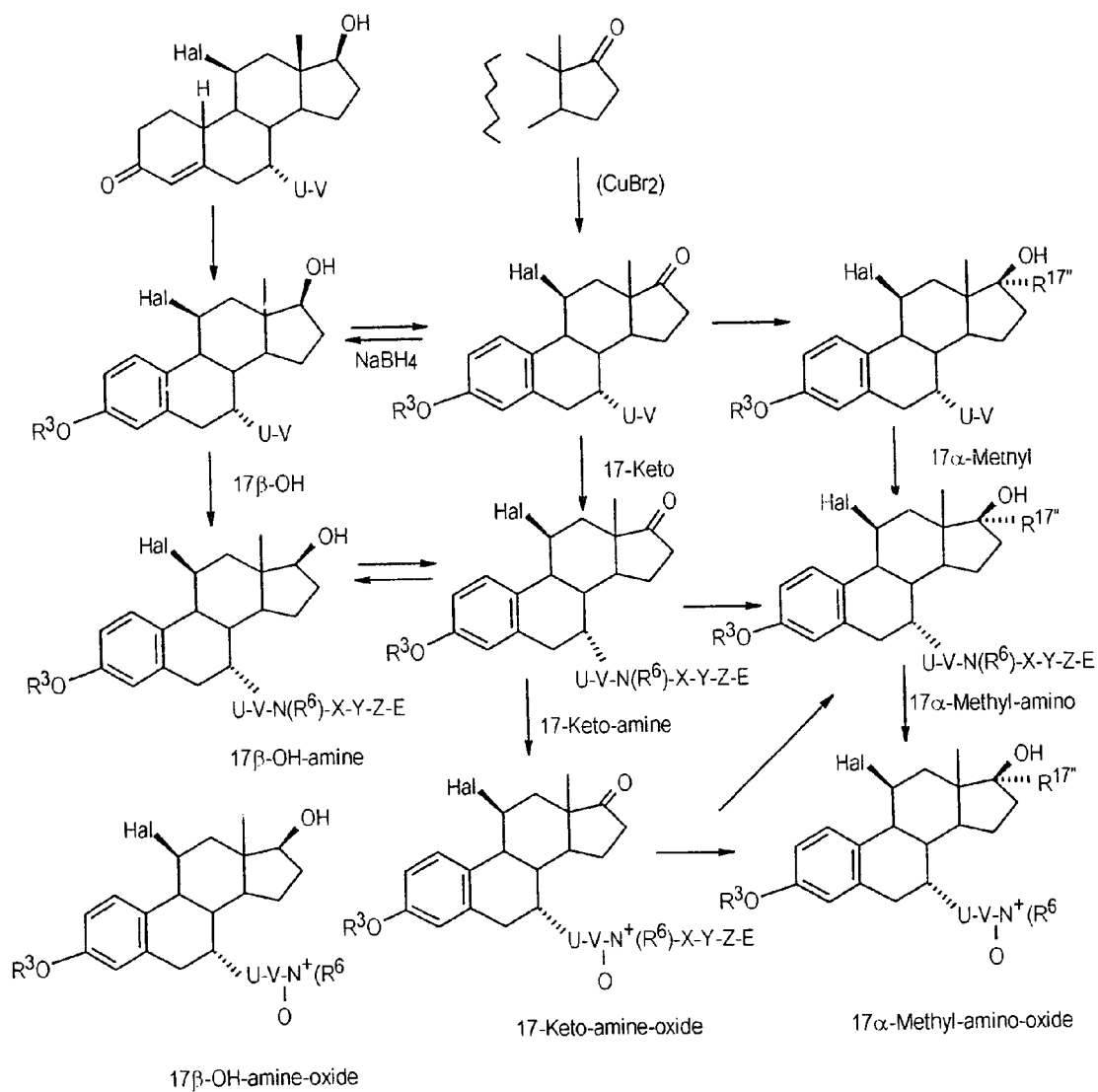
FIG. 1 Illustrates a reaction diagram according to which compounds of the intervention can be prepared.
Figure 2A:
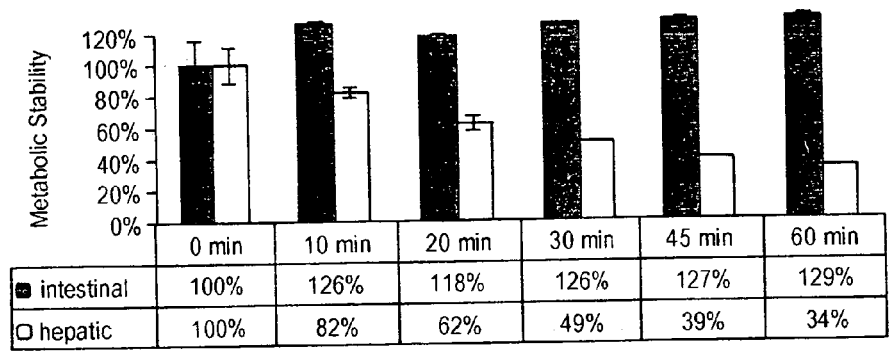
FIG. 2a-2f Illustrates the concentrations of test substances measured per LC/MS/MS and the resulting 17 ketone product.
Figure 2B:
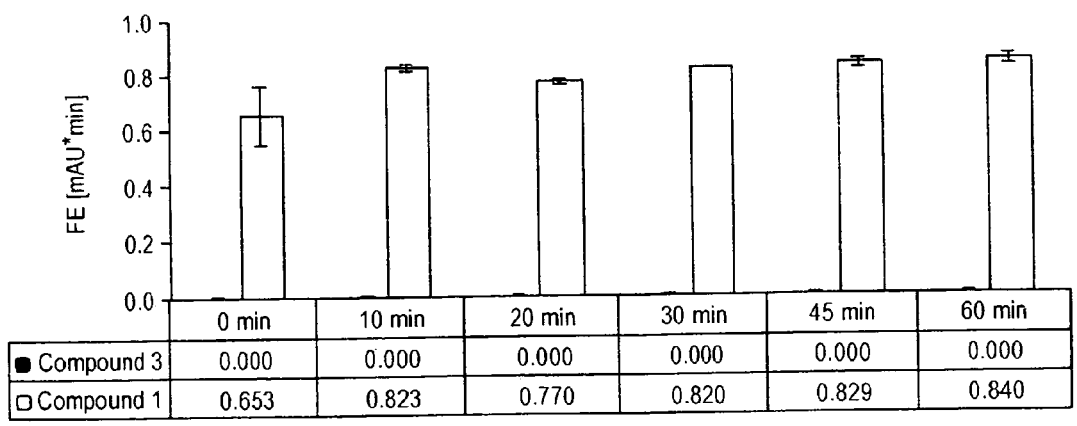
Figure 2C:
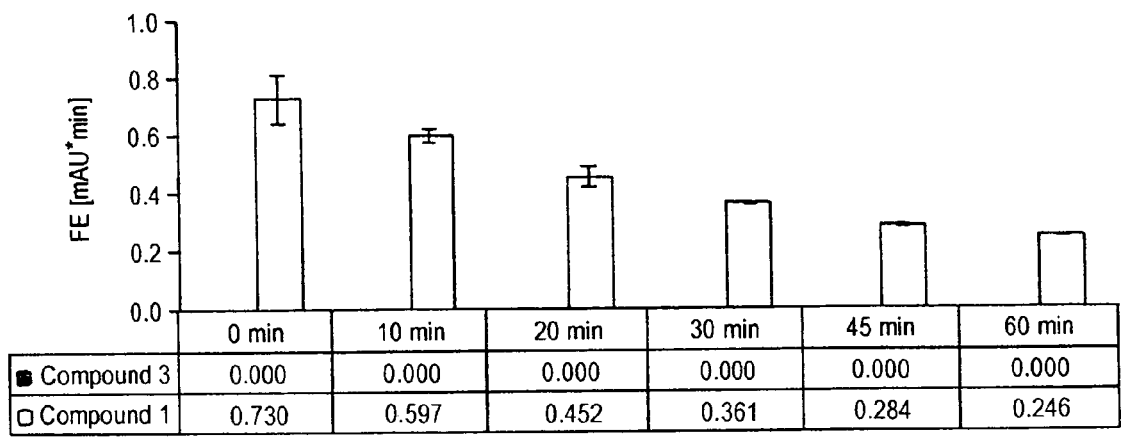
Figure 2D:
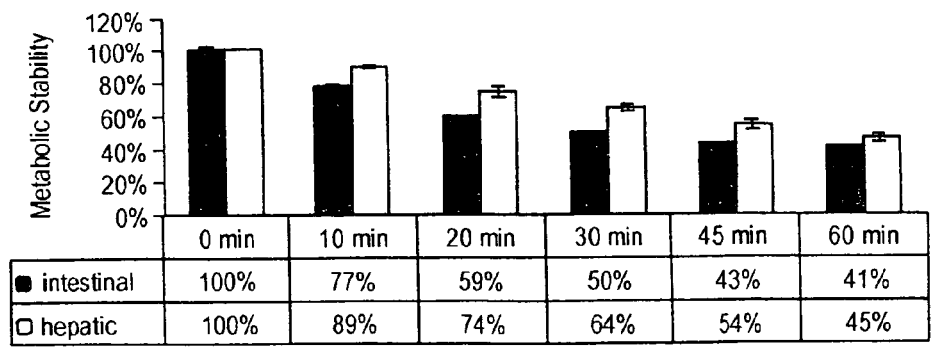
Figure 2E:
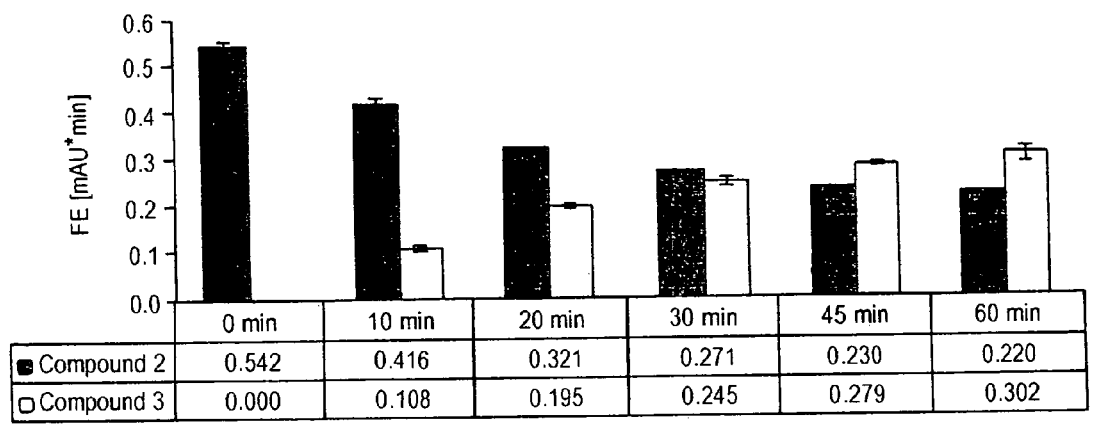
Figure 2F:
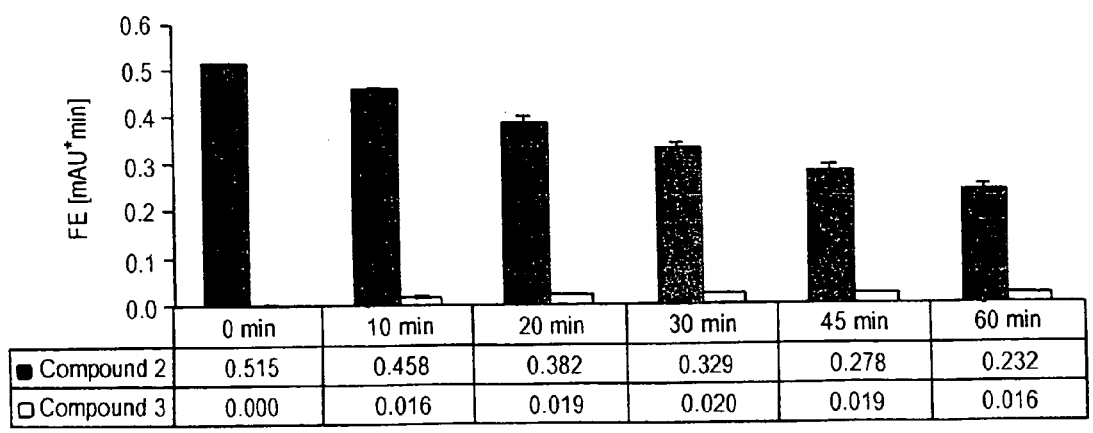

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

Process Variant 1.1

(Production of 17-oxo-estratrienes with amine-N-oxide Grouping in the Side Chain, Starting From 17β-hydroxy-estratrienes with an Amine Grouping in the Side Chain via the Corresponding 17-oxoestratrienes):

a) 11β-Fluoro-7α-{-[methyl(7,7,8,8,9,9,10,10,10-nonafluorodecyl)amino)-pentyl}estra-1,3,5(10)-trien-3-ol-17-one (Angle of Rotation $\alpha_D$ of this Compound (No. Z14) is Indicated in Table 5)

1.5 ml of ethyldiisopropylamine is added in drops at 10° C. to a solution of 1.23 g of pyridine sulfur trioxide complex in 10 ml of dried dimethyl sulfoxide. Then, 1.72 g of 11β-fluoro-7α-{5-[methyl(7,7,8,8,9,9,10,10,10-nonafluorodecyl) amino]pentyl}-estra-1,3,5(10)-triene-3,17β-diol (compound No. Z9) as well as another 10 ml of dried dimethyl sulfoxide are added and stirred for 30 minutes at room temperature. Then, it is diluted with ethyl acetate, washed with saturated sodium bicarbonate solution, water and sodium chloride solution, dried on sodium sulfate, evaporated to the dry state in a vacuum and chromatographed on silica gel with dichloromethane/methanol. 11β-Fluoro-7α-{5-[methyl(7,7,8,8,9, 9,10,10,10-nonafluorodecyl)amino]pentyl} estra-1,3,5(10)-trien-3-ol-17-one, $[\alpha]_D$=+58.2°, in chloroform, is obtained.

b) 11β-Fluoro-7α-{5-[methyl(7,7,8,8,9,9,10,10,10-nonafluorodecyl)amino]-pentyl} estra-1,3,5(10)-trien-3-ol-17-one N-oxide A solution of 0.5 g of 11β-fluoro-7α-{5-[methyl(7,7,8,8, 9,9,10,10,10-nonafluorodecyl)amino]pentyl} estra-1,3,5 (10)-trien-3-ol-17-one in 11 ml of methanol and 11 ml of chloroform is mixed with 3.5 ml of 30% hydrogen peroxide solution and stirred for five days at room temperature. Then, it is mixed with sodium thiosulfate, added to water, extracted three times with dichloromethane, washed neutral, dried on sodium sulfate, evaporated to the dry state in a vacuum and chromatographed on silica gel with dichloromethane/methanol. 401 mg of 11β-fluoro-7α-{5-[methyl(7,7,8,8,9,9,10,10, 10-nonafluorodecyl)amino]pentyl} estra-1,3,5(10)-trien-3-ol-17-one N-oxide is obtained as a solid with a melting point of 84-86° C.; $[\alpha]_D$=+53.6°, in chloroform.

c) 11β-Fluoro-7α-{5-[methyl(7,7,8,8,9,9,10,10,10-nonafluorodecyl)amino]-pentyl} 17α-methylestra-1,3,5(10)-triene-3,17-diol N-oxide A suspension of 2.3 g of cerium(III) chloride in 23 ml of tetrahydrofuran is mixed at 0° C. with 3.19 ml of a 3-molar methylmagnesium bromide solution in diethyl ether, and it is stirred for 30 minutes. A solution of 250 mg of 11β-fluoro-7α-{5-[methyl(7,7,8,8,9,9,10,10,10-nonafluorodecyl) amino]pentyl} estra-1,3,5(10)-trien-3-ol-17-one N-oxide in 5 ml of tetrahydrofuran is added in drops thereto and then stirred for 24 hours at room temperature, mixed at 0° C. with 10 ml of ammonium chloride solution, extracted with ethyl acetate, washed with water, dried with sodium sulfate, concentrated by evaporation in a vacuum, taken up with 5 ml of methanol and 5 ml of chloroform, mixed with 2 ml of 30% hydrogen peroxide solution, mixed and stirred for 5 days at room temperature. Then, it is mixed with sodium thiosulfate, added to water, extracted three times with dichloromethane, washed neutral, dried on sodium sulfate, evaporated to the dry state in a vacuum and chromatographed on silica gel with dichloromethane/methanol. 165 mg of 11β-fluoro-7α-{5-[methyl(7,7,8,8,9,9,10,10,10-nonafluorodecyl)amino]pentyl}-17α-methylestra-1,3,5(10)-triene-3,17β-diol N-oxide with a melting point of 122° C. is obtained.

Process Variant 1.2:

(Production of 17-oxo-estratrienes with amine-N-oxide Groupings in the Side Chain, Starting From 17β-hydroxy-estratrienes with Amine Groupings in the Side Chain via the Corresponding 17β-hydroxy-estratrienes with amine-N-oxide Groupings in the Side Chain):

a) 11β-Fluoro-7α-{5-[methyl(7,7,8,8,9,9,10,10,10-nonafluorodecyl)-amino]pentyl}-estra-1,3,5(10)-triene-3,17-diol N-oxide A solution of 50 g of 11β-fluoro-7α-{5-[methyl(7,7,8,8,9, 9,10,10,10-nonafluorodecyl)amino]pentyl}-estra-1,3,5(10)-triene-3,17β-diol in 500 ml of methanol and 500 ml of chloroform is mixed with 7.3 g of sodium bicarbonate as well as 45 ml of 30% hydrogen peroxide solution, and it is stirred for 3 days at room temperature. Then, it is mixed with sodium thiosulfate, added to water, extracted three times with dichloromethane, washed neutral, dried on sodium sulfate, evaporated to the dry state in a vacuum and absorptively precipitated from diethyl ether. 48.3 g of 11β-fluoro-7α-{5-[methyl (7,7,8,8,9,9,10,10,10-nonafluorodecyl)amino]pentyl}-estra-1,3,5(10)-triene-3,17β-diol N-oxide with a melting point of 131.7° C. is obtained.

b) 11β-Fluoro-7α-{5-[methyl(7,7,8,8,9,9,10,10,10-nonafluorodecyl)-amino]pentyl}-estra-1,3,5(10)-trien-3-ol-17 one N-oxide 1.5 ml of ethyldiisopropylamine is added in drops at 10° C. to a solution of 1.23 g of pyridine sulfur trioxide complex in 10 ml of dried dimethyl sulfoxide. Then, 1.62 g of 11β-fluoro-7α-{5-[methyl(7,7,8,8,9,9,10,10,10-nonafluorodecyl) amino]pentyl}-estra-1,3,5(10)-triene-3,17β-diol N-oxide as well as another 10 ml of dried dimethyl sulfoxide are added and stirred for 30 minutes at room temperature. Then, it is diluted with ethyl acetate, washed with saturated sodium bicarbonate solution, water and sodium chloride solution, dried on sodium sulfate, evaporated to the dry state in a vacuum and chromatographed on silica gel with dichloromethane/methanol. 1.32 g of 11β-fluoro-7α-{5-[methyl(7, 7,8,8,9,9,10,10,10-nonafluorodecyl)amino]pentyl}-estra-1, 3,5(10)-trien-3-ol-17one N-oxide is obtained as a solid with a melting point of 84-86° C.; $[\alpha]_D$=+53.6° in chloroform.

Process Variant 2.1:

(Production of 17β-methyl-estratrienes with amine-N-oxide Groupings in the Side Chain Starting from 17-oxo-estratrienes with Amine Groupings in the Side Chain via the Corresponding 17-oxo-estratrienes with amine-N-oxide Groupings in the Side Chain):

a) 11β-Fluoro-7α-{5-[methyl(7,7,8,8,9,9,10,10,10-nonafluorodecyl)amino]-pentyl}-17α-methylestra-1, 3,5(10)-triene-3,17β-diol (Physical Properties of This Compound (No. 7) are Indicated in Table 1)

A suspension of 230 g of cerium(III) chloride in 2.3l of tetrahydrofuran is mixed at 0° C. with 320 ml of a 3-molar methylmagnesium bromide solution in diethyl ether and stirred for 30 minutes. A solution of 25 g of 11β-fluoro-7α-{5-[methyl(7,7,8,8,9,9,10,10,10-nonafluorodecyl)amino]pentyl}estra-1,3,5(10)-trien-3-ol-17-one (angle of rotation $\alpha_D$ of this compound (No. Z14) is indicated in Table 5) in 250 ml of tetrahydrofuran is added in drops thereto and then stirred for 24 hours at room temperature, mixed at 0° C. with ammonium chloride solution, extracted with ethyl acetate, washed with water, dried with sodium sulfate, concentrated by evaporation in a vacuum and chromatographed on silica gel with dichloromethane/methanol. 19.1 g of 11β-fluoro-7α-{5-[methyl(7,7,8,8,9,9,10,10,10-nonafluorodecyl)amino]pentyl}-17α-methylestra-1,3,5(10)-triene-3,17β-diol with a melting point of 82-85° C. and $[\alpha]_D$=+21.80 in chloroform is obtained.

b) 11β-Fluoro-7α-{5-[methyl(7,7,8,8,9,9,10,10,10-nonafluorodecyl)-amino] pentyl}-17α-methylestra-1,3,5(10)-triene-3,17β-diol N-oxide A solution of 18 g of 11β-fluoro-7α-{5-methyl(7,7,8,8,9,9,10,10,10-nonafluorodecyl)amino]pentyl}-17α-methyl-estra-1,3,5(10)-triene-3,17β-diol in 180 ml of chloroform and 180 ml of methanol is mixed with 2.57 c of sodium bicarbonate and 16.2 ml of a 30% hydrogen peroxide solution, and it is stirred for 48 hours at room temperature. Then, it is diluted with dichloromethane, washed with water and sodium thiosulfate solution, dried on sodium sulfate, evaporated to the dry state in a vacuum and absorptively precipitated with diethyl ether. 18.4 g of 11β-fluoro-7α-{5-[methyl(7,7,8,8,9,9,10,10,10-nonafluorodecyl)amino]pentyl}-17α-methylestra-1,3,5(10)-triene-3,17β-diol N-oxide with a melting point of 122° C. is obtained.

Process Variant 2.2:

(Production of 17β-methyl-estratrienes with Amine Groupings in the Side Chain, Starting from 17-oxo-estratrienes via the Corresponding 17α-methyl-estratrienes):

a) 7α-(5-Bromopentyl)-11β-fluoro-17α-methylestra-1,3,5(10)-triene-3,17β-diol

A suspension of 46.8 g of cerium(III) chloride in 0.47 l of tetrahydrofuran is mixed at 0° C. with 63.8 ml of a 3-molar methylmagnesium bromide solution in diethyl ether, and it is stirred for 1 hour. A solution of 25 g of 7α-(5-bromopentyl)-11β-fluoro-estra-1,3,5(10)-trien-3-ol-17-one in 200 ml of tetrahydrofuran is added in drops thereto and then stirred for 28 hours at room temperature, mixed at 0° C. with ammonium chloride solution, extracted with ethyl acetate, washed with water, dried with sodium sulfate, concentrated by evaporation in a vacuum and chromatographed on silica gel with dichloromethane/methanol. 15.1 g of 7α-(5-bromopentyl)-11β-fluoro-17α-methylestra-1,3,5(10)-triene-3,17β-diol with a melting point of 48.6° C. is obtained.

b) 11β-Fluoro-7α-{5-[methyl(7,7,8,8,9,9,10,10,10-nonafluorodecyl)amino]-pentyl}-17α-methylestra-1,3,5(10)-triene-3,17β-diol (Physical Properties of This Compound (No. 7) are Indicated in Table 1)

A solution of 18 g of 7α-(5-bromopentyl)-1-fluoro-17α-methylestra-1,3,5(10)-triene-3,17-diol in 180 ml of dimethylformamide is mixed with 15.9 g of (7,7,8,8,9,9,10,10,10-nonafluorodecyl)-methyl-amine and 5 g of sodium carbonate and then stirred for 8.5 hours at a bath temperature of 80° C. Then, it is added to water, extracted with ethyl acetate, washed with water and saturated sodium chloride solution, dried on sodium sulfate, concentrated by evaporation in a vacuum and chromatographed on silica gel with dichloromethane/methanol. 22.9 g of 11β-fluoro-7α-{5-[methyl(7,7,8,8,9,9,10,10,10-nonafluorodecyl)amino]pentyl}-17α-methylestra-1,3,5(10)-triene-3,17β-diol with a melting point of 82-85° C. and $[\alpha]_D$=+21.8° in chloroform is obtained.

Additional compounds according to the invention can be produced analogously. To this end, additional intermediate products are presented in Table D. In addition, physical properties of these compounds are also partially indicated.

TABLE 1

| | | Melting Point [° C.] | Angle of Rotation $\alpha_D{}^1$) |
|---|---|---|---|
| 1 | 11β-Fluoro-7α-{5-[methyl(7,7,8,8,9,9,9-heptafluorononyl)amino]pentyl}-17α-methylestra-1,3,5(10)-triene-3,17β-diol N-oxide | 152-154 | |
| 2 | 11β-Fluoro-7α-{5-[methyl(8,8,9,9,10,10,10-heptafluorodecyl)amino]pentyl}-17α-methylestra-1,3,5(10)-triene-3,17β-diol N-oxide | 137.7 | +31° |
| 3 | (RS)-11β-Fluoro-7α-{5-[methyl(7,7,8,8,9,9,10,10,10-nonafluorodecyl)amino]pentyl}-17α-methylestra-1,3,5(10)-triene-3,17β-diol N-oxide | 122 | +29.6° |
| 4 | 11β-Fluoro-7α-{5-[methyl(8,8,9,9,9-pentafluorononyl)amino]pentyl}-17α-methylestra-1,3,5(10)-triene-3,17β-diol N-oxide | 148.5 | +25.3° |
| 5 | 11β-Fluoro-7α-{5-[methyl(9,9,10,10,10-pentafluorodecyl)amino]pentyl-17α-methylestra-1,3,5(10)-triene-3,17β-diol N-oxide | 118-120 | +26° |
| 6 | 11β-Fluoro-7α-{5-[methyl(8,8,9,9,9-pentafluorononyl)amino]pentyl}-17α-methylestra-1,3,5(10)-triene-3,17β-diol | 68-71 | +32° |
| 7 | 11β-Fluoro-7α-{5-[methyl(7,7,8,8,9,9,10,10,10-nonafluorodecyl)amino]pentyl}-17α-methylestra-1,3,5(10)-triene-3,17β-diol | 82-85 | +21.8 |
| 8 | 11β-Fluoro-7α-{5-[methyl(7,7,8,8,9,9,9-heptafluorononyl)amino]pentyl}-17α-methylestra-1,3,5(10)-triene-3,17β-diol | 138 | +29.8° |
| 9 | 17α-Ethinyl-11β-fluoro-7α-{5-[methyl(7,7,8,8,9,9,10,10,10-nonafluorodecyl)amino]pentyl}-estra-1,3,5(10)-triene-3,17β-diol | 128-130 | +13.1° |
| 10 | 17α-Ethinyl-11β-fluoro-3-(2-tetrahydropyranoyloxy)-7α-{5-[methyl(7,7,8,8,9,9,10,10,10-nonafluorodecyl)amino]pentyl}-estra-1,3,5(10)-trien-17β-ol | | +18.1° |
| 11 | 11β-Fluoro-3-(2-tetrahydropyranyloxy)-7α-{5-[methyl(7,7,8,8,9,9,10,10,10-nonafluorodecyl)amino]pentyl}-17α-methylestra-1,3,5(10)-trien-17β-ol | | +26.9° |

TABLE 1-continued

| | Melting Point [° C.] | Angle of Rotation $\alpha_D$[1] |
|---|---|---|
| 12 11β-Fluoro-7α-{5-[methyl(7,7,8,8,9,9,10,10,10-nonafluorodecyl)amino]pentyl}-17α-trifluoromethylestra-1,3,5(10)-triene-3,17β-diol | | +24.6° |
| 13 11β-Fluoro-7α-{5-[methyl(6,6,7,7,8,8-heptafluorooctyl)amino]pentyl}-17α-methylestra-1,3,5(10)-triene-3,17β-diol | 96.3 | +38.8° |
| 14 11β-Fluoro-7α-{5-[methyl(8,8,9,9,10,10,10-heptafluorodecyl)amino]pentyl}-17α-methylestra-1,3,5(10)-triene-3,17β-diol | 137 | +24.6° |
| 15 11β-Fluoro-7α-{5-[methyl(6,6,7,7,8,8,9,9,10,10,10-undecafluorodecyl)amino]pentyl}-17α-methylestra-1,3,5(10)-triene-3,17β-diol | 112.6 | +21.3° |
| 16 11β-Fluoro-7α-{5-[methyl(5,5,6,6,7,7,8,8,8-nonafluorooctyl)amino]pentyl}-17α-methylestra-1,3,5(10)-triene-3,17β-diol | | |
| 17 11β-Fluoro-7α-{5-[methyl(9,9,10,10,11,11,11-heptafluoroundecyl)amino]pentyl}-17α-methylestra-1,3,5(10)-triene-3,17β-diol | | |
| 18 11β-Fluoro-7α-{5-[methyl(9,9,10,10,10-pentafluorodecyl)amino]pentyl}-17α-methylestra-1,3,5(10)-triene-3,17β-diol | 88-90 | +32.5° |

[1])$[\alpha]_D$ in Chloroform

TABLE 2

| | Antiuterotropic Action | | | |
|---|---|---|---|---|
| | s.c. | % Inhib. | p.o. | % Inhib. |
| 3 (RS)-11β-Fluoro-7α-{5-[methyl(7,7,8,8,9,9,10,10,10-nonafluorodecyl)amino]pentyl}-17α-methylestra-1,3,5(10)-triene-3,17β-diol N-oxide | | | 0.3 | 76 |
| 7 11β-Fluoro-7α-{5-[methyl(7,7,8,8,9,9,10,10,10-nonafluorodecyl)amino]pentyl}-17α-methylestra-1,3,5(10)-triene-3,17β-diol | 0.03 | 59 | | |
| 8 11β-Fluoro-7α-{5-[methyl(7,7,8,8,9,9,9-heptafluorononyl)amino]pentyl}-17α-methylestra-1,3,5(10)-triene-3,17β-diol | | | 0.3 | 94 |

TABLE 3

| | Melting Point [° C.] | Angle of Rotation $\alpha_D$[1] |
|---|---|---|
| X1 11β-Fluoro-7α-{5-[methyl(8,8,9,9,9-pentafluorononyl)amino]pentyl}estra-1,3,5(10)-triene-3,17β-diol N-oxide | 158-160 | +33.6° |
| X2 11β-Fluoro-7α-[5-(methyl{3-[(2,3,4,5,6-pentafluorophenyl)sulfanyl]propyl}amino)-pentyl]estra-1,3,5(10)-triene-3,17β-diol N-oxide | | |
| X3 11β-Fluoro-7α-[5-(methyl{3-[(4,4,5,5,5-pentafluoropentyl)sulfanyl]propyl}amino)-pentyl]estra-1,3,5(10)-triene-3,17β-diol N-oxide | 114-116 | |
| X4 11β-Fluoro-7α-[5-(methyl{3-[(4,4,5,5,5-pentafluoropentyl)sulfinyl]propyl}-amino)pentyl]estra-1,3,5(10)-triene-3,17β-diol N-oxide | 103-105 | |
| X5 11β-Fluoro-7α-{5-[methyl(7,7,8,8,9,9,10,10,10-nonafluorodecyl)amino]pentyl}estra-1,3,5(10)-triene-3,17β-diol N-oxide | 147-150 | +30.2° |
| X6 (S)-11β-Fluoro-7α-{5-[methyl(7,7,8,8,9,9,10,10,10-nonafluorodecyl)amino]pentyl}-17α-methylestra-1,3,5(10)-triene-3,17β-diol N-oxide | 128.5 | +32.5° |
| X7 (R)-11β-Fluoro-7α-{5-[methyl(7,7,8,8,9,9,10,10,10-nonafluorodecyl)amino]pentyl}-17α-methylestra-1,3,5(10)-triene-3,17β-diol N-oxide | 144.0 | +31.3° |
| X8 11β-Fluoro-7α-{5-[methyl(9,9,10,10,10-pentyfluorodecyl)amino]pentyl}estra-1,3,5(10)-triene-3,17β-diol N-oxide | 99-101 | +28.5° |

[1])$[\alpha]_D$ in chloroform

TABLE 4

|  |  | Melting Point [° C.] | Angle of Rotation $\alpha_D$[1]) |
|---|---|---|---|
| Y1 | 11β-Fluoro-7α-[5-(methyl{3-[(4,4,5,5,5-pentafluoropentyl)sulfinyl]propyl}amino)-pentyl]estra-1,3,5(10)-trien-3-ol-17-one N-oxide |  | +45.6° |
| Y2 | 11β-Fluoro-7α-[5-(methyl{3-[(4,4,5,5,5-pentafluoropentyl)sulfanyl]propyl}amino)-pentyl]estra-1,3,5(10)-trien-3-ol-17-one N-oxide |  | +52.8° |
| Y3 | 11β-Fluoro-7α-{5-[methyl(7,7,8,8,9,9,10,10,10-nonafluorodecyl)amino]pentyl}estra-1,3,5(10)-trien-3-ol-17-one N-oxide | 84–86 | +53.6° |

[1]) $[\alpha]_D$ in chloroform

TABLE 5

|  |  | Melting Point [° C.] | Angle of Rotation $\alpha_D$[1]) |
|---|---|---|---|
| Z1 | 11β-Fluoro-7α-{5-[methyl(8,8,9,9,9-pentafluorononyl)amino]pentyl}estra-1,3,5(10)-triene-3,17β-diol |  |  |
| Z2 | 11β-Fluoro-7α-{5-[methyl(8,8,9,9,9-pentafluorononyl)amino]pentyl}estra-1,3,5(10)-trien-3-ol-17-one |  |  |
| Z3 | 11β-Fluoro-7α-{5-[methyl(3,3,4,4,5,5,6,6,7,7,8,8,8-tridecafluorooctyl)amino]pentyl}estra-1,3,5(10)-trien-3-ol-17-one |  |  |
| Z4 | 11β-Fluoro-7α-{5-[methyl(9,9,10,10,10-pentafluorodecyl)amino]pentyl}estra-1,3,5(10)-trien-3-ol-17-one |  | +48.4° |
| Z5 | 11β-Fluoro-7α-{5-[methyl(9,9,10,10,10-pentafluorodecyl)amino]pentyl}estra-1,3,5(10)-triene-3,17β-diol |  |  |
| Z6 | 11β-Fluoro-7α-{5-[methyl(3,3,4,4,5,5,6,6,6-nonafluorohexyl)amino]pentyl}estra-1,3,5(10)-triene-3,17β-diol |  |  |
| Z7 | 11β-Fluoro-7α-{5-[methyl(4,4,5,5,6,6,7,7,8,8,9,9,9-tridecafluorononyl)amino]pentyl}-estra-1,3,5(10)-triene-3,17β-diol |  |  |
| Z8 | 11β-Fluoro-7α-{5-[methyl(7,7,8,8,8-pentafluorooctyl)amino]pentyl}estra-1,3,5(10)-triene-3,17β-diol |  |  |
| Z9 | 11β-Fluoro-7α-{5-[methyl(7,7,8,8,9,9,10,10,10-nonafluorodecyl)amino]penty}estra-1,3,5(10)-triene-3,17β-diol |  |  |
| Z10 | 11β-Fluoro-7α-{5-[methyl(7,7,8,8,9,9,10,10,11,11,12,12,12-tridecafluorododecyl)amino]-pentyl}estra-1,3,5(10)-triene-3,17β-diol |  |  |
| Z11 | 11β-Fluoro-7α-{5-[methyl(4,4,5,5,6,6,7,7,8,8,9,9,10,10,11,11,11-heptadecafluoroundecyl)amino]pentyl}estra-1,3,5(10)-triene-3,17β-diol |  |  |
| Z12 | 11β-Fluoro-7α-{5-[methyl(7,7,8,8,9,9,10,10,11,11,12,12,13,13,14,14,14-heptadecafluorotetradecyl)amino]pentyl}estra-1,3,5(10)-triene-3,17β-diol |  |  |
| Z13 | 11β-Fluoro-7α-{5-[methyl(5,5,6,6,7,7,8,8,9,9,10,10,10-tridecafluorodecyl)amino]pentyl}-estra-1,3,5(10)-triene-3,17β-diol |  |  |
| Z14 | 11β-Fluoro-7α-{5-[methyl(7,7,8,8,9,9,10,10,10-nonafluorodecyl)amino]pentyl}estra-1,3,5(10)-trien-3-ol-17-one |  | +58.2° |
| Z15 | 11β-Fluoro-3-methoxy-7α-{5-[methyl(7,7,8,8,9,9,10,10,10-nonafluorodecyl)amino]-pentyl}estra-1,3,5(10)-trien-17β-ol |  | +39.2° |
| Z16 | 11β-Fluoro-3-methoxy-7α-{5-[methyl(7,7,8,8,9,9,10,10,10-nonafluorodecyl)amino]-pentyl}estra-1,3,5(10)-trien-17-one |  | +55.9° |
| Z17 | 17β-Acetyloxy-11β-fluoro-7α-{5-[methyl(7,7,8,8,9,9,10,10,10-nonafluorodecyl)amino]-pentyl}estra-1,3,5(10)-trien-3-ol |  | +21.0° |
| Z18 | 11β-Fluoro-7α-{5-[methyl(7,7,8,8,9,9,10,10,10-nonafluorodecyl)amino]pentyl}estra-1,3,5(10)-triene-3-(2-tetrahydropyranoyloxy)-17-one |  | +66.1° |
| Z19 | 3-tert-Butanoyloxy-11β-fluoro-7α-{5-[methyl(7,7,8,8,9,9,10,10,10-nonafluorodecyl)-amino]pentyl}estra-1,3,5(10)-trien-17β-ol |  | +31.2° |
| Z20 | 3-Acetyloxy-11β-fluoro-7α-{5-[methyl(7,7,8,8,9,9,10,10,10-nonafluorodecyl)amino]-pentyl}estra-1,3,5(10)-trien-17β-ol |  | +33° |
| Z21 | 11β-Fluoro-7α-{5-[methyl(6,6,7,7,8,8,9,9,9-nonafluorononyl)amino]pentyl}estra-1,3,5(10)-triene-3,17β-diol |  |  |
| Z22 | 11β-Fluoro-7α-{5-[methyl(8,8,9,9,10,10,11,11,11-nonafluoroundecyl)amino]pentyl}estra-1,3,5(10)-triene-3,17β-diol |  |  |
| Z23 | 11β-Fluoro-7α-{5-[methyl(7,7,8,8,9,9,9-heptafluorononyl)amino]pentyl}estra-1,3,5(10)-triene-3,17β-diol | 125.0 |  |
| Z24 | 11β-Fluoro-7α-{5-[methyl(7,7,8,8,9,9,9-heptafluorononyl)amino]pentyl}estra-1,3,5(10)-trien-3-ol-17-one |  | +70.2° |
| Z25 | 11β-Fluoro-7α-{5-[methyl(6,6,7,7,8,8,8-heptafluorooctyl)amino]pentyl}estra-1,3,5(10)-trien-3-ol-17-one |  | +71.6° |
| Z26 | 11β-Fluoro-7α-{5-[methyl(6,6,7,7,8,8,8-heptafluorooctyl)amino]pentyl}estra-1,3,5(10)-triene-3,17β-diol | 112.8 | +42.6° |
| Z27 | 11β-Fluoro-7α-{5-[methyl(8,8,9,9,10,10,10-heptafluorodecyl)amino]pentyl}estra-1,3,5(10)-trien-3-ol-17-one |  | +56.2° |
| Z28 | 11β-Fluoro-7α-{5-[methyl(8,8,9,9,10,10,10-heptafluorodecyl)amino]pentyl}estra-1,3,5(10)-triene-3,17β-diol | 104 | +34.9° |
| Z29 | 11β-Fluoro-7α-{5-[methyl(6,6,7,7,8,8,9,9,10,10,10-undecafluorodecyl)amino]-pentyl}estra-1,3,5(10)-trien-3-ol-17-one |  | +64.6° |

TABLE 5-continued

| | | Melting Point [° C.] | Angle of Rotation $\alpha_D{}^1$) |
|---|---|---|---|
| Z30 | 11β-Fluoro-7α-{5-[methyl(6,6,7,7,8,8,9,9,10,10,10-undecafluorodecyl)amino]-pentyl}estra-1,3,5(10)-triene-3,17β-diol | 94-96 | +36.8° |
| Z31 | 11β-Fluoro-7α-{5-[methyl(5,5,6,6,7,7,8,8,8-nonafluorooctyl)amino]pentyl}estra-1,3,5(10)-trien-3-ol-17-one | | |
| Z32 | 11β-Fluoro-7α-{5-[methyl(5,5,6,6,7,7,8,8,8-nonafluorooctyl)amino]pentyl}estra-1,3,5(10)-triene-3,17β-diol | | |
| Z33 | 11β-Fluoro-7α-{5-[methyl(9,9,10,10,11,11,11-heptafluoroundecyl)amino]pentyl}estra-1,3,5(10)-trien-3-ol-17-one | | |
| Z34 | 11β-Fluoro-7α-{5-[methyl(9,9,10,10,11,11,11-heptafluoroundecyl)amino]pentyl}estra-1,3,5(10)-triene-3,17β-diol | | |

[1])[$\alpha_D$] in chloroform

The entire disclosure of all applications, patents and publications, cited herein and of corresponding German Application No. 101 59 217.5, filed Nov. 27, 2001 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A 17β-Alkyl-17β-oxy-estratrienes of formula I

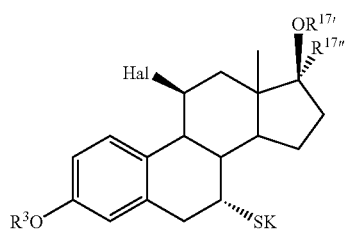

I in which
Hal stands for F or Cl, and is in 11β-position,
$R^3$ stands for hydrogen, $C_1$-$C_4$-alkyl, $C_1$-$C_4$-alkanoyl or a cyclic $C_3$-$C_7$-ether with the O atom,
$R^{17'}$ stands for hydrogen, $C_1$-$C_4$-alkyl or $C_1$-$C_4$-alkanoyl,
$R^{17''}$ stands for $C_1$-$C_4$-alkyl, $C_1$-$C_4$-alkinyl, $C_1$-$C_4$-alkinyl as for at least partially fluorinated $C_1$-$C_4$-alkyl,
wherein $R^{17'}$—O in 17β-position and $R^{17''}$ in 17α-position
SK stands for U-V-W-X-Y-Z-E, which is bonded via U in 7α-position,
U represents either a straight-chain or branched-chain $C_1$-$C_{13}$-alkylene- alkenylene- or -alkinylene radical or the group A-B, whereby A is bonded in the 7α-position and represents a benzylidene radical that is bonded via —CH$_2$— in the 7α-position, a phenylene radical, or a $C_1$-$C_3$-alkylaryl radical that is bonded via the alkyl group in the 7α-position, and B stands for a straight-chain or branched-chain $C_1$-$C_{13}$-alkylene, or $C_2$-$C_{13}$-alkenylene- or -alkinylene radical, and wherein A and B are optionally connected to one another via an O atom,
V represents a CH$_2$— or a C(O) group,
W is an N(R$^6$)— group or an N$^+$(O$^-$)(R$^6$) group or an azolidinylene ring or an azolidinylene-N-oxide ring, wherein the azolidinylene ring or azolidinylene-N-oxide ring includes at least one C atom of grouping X,
$R^6$ is either H or CH$_2$—R$^7$ or C(O)—R$^7$,
$R^7$ is
 a) hydrogen or
 b) a straight-chain or branched-chain, non-fluorinated or at least partially fluorinated $C_1$-$C_{14}$-alkyl, $C_2$-$C_{14}$-alkenyl- or -alkinyl radical, any of which can be hydroxylated in one or more places and can be interrupted by one to three of the heteroatoms —O—, —S— and/or —NR$^9$—, in which R$^9$ stands for hydrogen or a $C_1$-$C_3$-alkyl radical, or
 c) an unsubstituted or substituted aryl- or heteroaryl radical or
 d) an unsubstituted or substituted $C_3$-$C_{10}$-cycloalkyl radical or
 e) an unsubstituted or substituted $C_4$-$C_{15}$-cycloalkylalkyl radical or
 f) an unsubstituted or substituted $C_7$-$C_{20}$-aralkyl radical or
 g) an unsubstituted or substituted heteroaryl-$C_1$-$C_6$-alkyl radical or
 h) an unsubstituted or substituted aminoalkyl radical or a biphenyl radical,
X is a direct bond between W and Y or is a straight-chain or branched-chain $C_1$-$C_{12}$-alkylene, $C_2$-$C_{12}$-alkenylene- or -alkinylene radical, in which
Y is
 1) a direct bond between X and Z, or
 2) when W is an N$^+$(O$^-$)(R$^6$) group or an azolidinylene—N—oxide ring an SO$_n$—R$^{10}$ group, wherein n=0, 1 or 2,
  wherein $R^{10}$ represents a direct bond between SO$_n$ and Z or a straight-chain or branched-chain $C_1$-$C_6$-alkylene-, $C_2$-$C_6$-alkenylene- or -alkinylene radical, or
 3) $R^{11}$ or O—$R^{11}$, wherein $R^{11}$ stands for
  i) a straight-chain or branched-chain $C_1$-$C_5$-alkylene-, $C_2$-$C_5$-alkenylene- or -alkinylene radical or for
  ii) an unsubstituted or substituted aryl radical or heteroaryl radical or for iii) an unsubstituted or substituted $C_3$-$C_{10}$-cycloalkyl radical or for iv) an unsubstituted or substituted $C_4$-$C_{15}$-cycloalkylalkyl radical or for v) an unsubstituted or substituted $C_7$-$C_{20}$-aralkyl radical or for vi) an unsubstituted or substituted heteroaryl-$C_1$-$C_6$-alkyl radical, or 4) CH=CF or 5) HN—C(O)—NH—$R^{12}$, wherein $R^{12}$ stands for an unsubstituted or substituted arylene radical, and wherein $R^{12}$ is bonded to Z, Z is a direct bond between Y and E or a straight-chain or branched-chain $C_1$-$C_9$-alkylene-, $C_2$-$C_6$-alkenylene- or -alkinylene radical, which is optionally partially or completely fluorinated, E is a $CF_3$ group or an at least partially fluorinated aryl group, or a pharmacologically compatible acid addition salt or ester thereof.

2. An estratrienes according to claim 1, wherein $R^3$ stands for hydrogen, $CH_3$, $CH_3CO$ or $C_5H_{10}O$.

3. An estratrienes according to claim 1, wherein $R^{17'}$ stands for hydrogen, $CH_3$ or $CH_3CO$, and wherein $R^{17''}$ stands for methyl, ethinyl or trifluoromethyl.

4. An estratrienes according to claim 1, wherein Hal stands for fluorine.

5. An estratrienes according to claim 1, wherein U stands for $(CH_2)_p$, whereby p is an integer from 2 to 10.

6. An estratrienes according to claim 5, wherein p=4.

7. An estratrienes according to claim 1, wherein V stands for $CH_2$.

8. An estratrienes according to claim 1, wherein W stands for $N(R^6)$— or $N^+(O^-)(R^6)$, whereby $R^6$ is hydrogen or a $C_1$-$C_3$-alkyl radical.

9. An estratrienes according to claim 1, wherein $R^6$ stands for methyl.

10. An estratrienes according to claim 1, wherein X stands for $(CH_2)_q$, whereby q=0 or is an integer from 1 to 12.

11. An estratrienes according to claim 1, wherein Y is a direct bond between X and Z or an $SO_n$ group, whereby n=0, 1 or 2.

12. An estratrienes according to claim 1, wherein Z is a straight-chain or branched-chain $C_1$-$C_7$-alkylene radical, which is at least partially fluorinated.

13. An estratrienes according to claim 1, wherein E stands for $CF_3$ or for pentafluorophenyl.

14. An estratrienes according to claim 1, wherein Z-E stands for $C_2F_5$, $C_3F_7$, $C_4F_9$ or for $C_6F_5$.

15. An estratrienes, which is

11β-Fluoro-7α-{5-[methyl(7,7,8,8,9,9,9-heptafluorononyl)amino]pentyl}-17α-methylestra-1,3,5(10)-triene-3,17β-diol N-oxide 11β-Fluoro-7α-{5-[methyl(8,8,9,9,10,10,10-heptafluorodecyl)amino]pentyl}-17α-methylestra-1,3,5(10)-triene-3,17β-diol N-oxide (RS)-11β-Fluoro-7α-{5-[methyl(7,7,8,8,9,9,10,10,10-nonafluorodecyl)amino]-pentyl}-17α-methylestra-1,3,5(10)-triene-3,17β-diol N-oxide 11β-Fluoro-7α-{5-[methyl(8,8,9,9,9-pentafluorononyl)amino]pentyl}-17α-methylestra-1,3,5(10)-triene-3,17β-diol N-oxide 11β-Fluoro-7α-{5-[methyl(9,9,10,10,10-pentafluorodecyl)amino]pentyl-17α-methylestra-1,3,5(10)-triene-3,17β-diol N-oxide 11β-Fluoro-7α-{5-[methyl(8,8,9,9,9-pentafluorononyl)amino]pentyl}-17α-methylestra-1,3,5(10)-triene-3,17β-diol 11β-Fluoro-7α-{5-[methyl(7,7,8,8,9,9,10,10,10-nonafluorodecyl)amino]pentyl}-17α-methylestra-1,3,5(10)-triene-3,17β-diol 11β-Fluoro-7α-{5-[methyl(7,7,8,8,9,9,9-heptafluorononyl)amino]pentyl}-17α-methylestra-1,3,5(10)-triene-3,17β-diol 17α-Ethinyl-11β-fluoro-7α-{5-[methyl(7,7,8,8,9,9,10,10,10-nonafluorodecyl)-amino]pentyl}-estra-1,3,5(10)-triene-3,17β-diol 17α-Ethinyl-11β-fluoro-3-(2-tetrahydropyranoyloxy)-7α-{5-[methyl(7,7,8,8,9,9,10,10,10-nonafluorodecyl)amino]pentyl}-estra-1,3,5(10)-trien-17β-ol 11β-Fluoro-3-(2-tetrahydropyranyloxy)-7α-{5-[methyl(7,7,8,8,9,9,10,10,10-nonafluorodecyl)amino]pentyl}-11β-methylestra-1,3,5(10)-trien-17β-ol 11β-Fluoro-7α-{5-[methyl(7,7,8,8,9,9,10,10,10-nonafluorodecyl)amino]pentyl}-17α-trifluoromethylestra-1,3,5(10)-triene-3,17β-diol 11β-Fluoro-7α-{5-[methyl(6,6,7,7,8,8,8-heptafluorooctyl)amino]pentyl}-17α-methylestra-1,3,5(10)-triene-3,17β-diol 11β-Fluoro-7α-{5-[methyl(8,8,9,9,10,10,10-heptafluorodecyl)amino]pentyl}-17α-methylestra-1,3,5(10)-triene-3,17β-diol 11β-Fluoro-7α-{5-[methyl(6,6,7,7,8,8,9,9,10,10,10-undecafluorodecyl)amino]-pentyl}-17α-methylestra-1,3,5(10)-triene-3,17β-diol 11β-Fluoro-7α-{5-[methyl(5,5,6,6,7,7,8,8,8-nonafluorooctyl)amino]pentyl} 17α-methylestra-1,3,5(10)-triene-3,17β-diol 11β-Fluoro-7α-{5-[methyl(9,9,10,10,11,11,11-heptafluoroundecyl)amino]pentyl}-17α-methylestra-1,3,5(10)-triene-3,17β-diol or 11β-Fluoro-7α-{5-[methyl(9,9,10,10,10-pentafluorodecyl)amino]pentyl}-17α-methylestra-1,3,5(10)-triene-3,17β-diol.

16. A compound according to claim 1, wherein W stands for an N+(O−)($R^6$) group or for an azolidinylene-N-oxide ring, wherein the azolidinylene-N-oxide ring includes at least one C atom of grouping X.

17. A compound according to claim 16, wherein Y is an $SO_n$-$R^{10}$ group.

18. A compound according to claim 1, wherein V is a C(O) group.

19. A compound according to claim 1, wherein W is an azolidinylene ring.

20. A compound according to claim 1, which is a salt of said compound.

21. An estratriene according to claim 1, which is or a pharmacologically compatible acid addition salt or ester thereof.

22. A estratriene according to claim 1, which is or a pharmacologically compatible acid addition salt thereof.

23. A compound according to claim 1, which is a salt of said compound.

24. A pharmaceutical composition comprising a compound of claim 1 and a pharmaceutically acceptable carrier.

25. 17β-Oxy-estratrienes of formula II in which
Hal stands for F or Cl and is bonded in 11β-position,
$R^3$ stands for hydrogen, $C_1$-$C_4$-alkyl, $C_1$-$C_4$-alkanoyl or a cyclic $C_3$-$C_7$-ether with the O atom,
$R^{17'}$ stands for hydrogen, $C_1$-$C_4$-alkyl or for $C_1$-$C_4$-alkanoyl and is bonded in 17β-position,
SK stands for the grouping U-V-W-X-Y-Z-E, which is bonded via U in 7α-position,
W stands for an $N^+(O^-)(R^6)$ group or for an azolidinylene-N-oxide ring, wherein the azolidinylene-N-oxide ring includes at least one C atom of grouping X,
$R^6$ is either H or $CH_2$-$R^7$ or C(O)-$R^7$,
$R^7$ is
  i) hydrogen or
  j) a straight-chain or branched-chain, non-fluorinated or at least partially fluorinated $C_1$-$C_{14}$-alkyl, $C_2$-$C_{14}$-alkenyl-or-alkinyl radical, any of which can be hydroxylated in one or more places and can be interrupted by one to three of the heteroatoms —O—,—S—and/or —$NR^9$, R-, in which $R^9$ stands for hydrogen or a $C_1$-$C_3$-alkyl radical, or k) an unsubstituted or substituted aryl- or heteroaryl radical or
  l) an unsubstituted or substituted $C_3$-$C_{10}$-cycloalkyl radical or
  m) an unsubstituted or substituted $C_4$-$C_{13}$-cycloalkylalkyl radical or
  n) an unsubstituted or substituted $C_7$-$C_{20}$-aralkyl radical or
  o) an unsubstituted or substituted heteroaryl-$C_1$-$C_6$-alkyl radical or
  p) an unsubstituted or substituted aminoalkyl radical or a biphenyl radical,
U represents either a straight-chain or branched-chain $C_1$-$C_{13}$-alkylene, or $C_2$-$C_{13}$-alkenylene- or -alkinylene radical or the group A-B, wherein A is bonded in the 7α-position and represents a benzylidene radical that is bonded via -$CH_2$- in the 7α-position, a phenylene radical, or a $C_1$-$C_3$-alkylaryl radical that is bonded via the alkyl group in the 7α-position, and B stands for a straight-chained or branched-chain $C_1$-$C_{13}$-alkylene, or $C_2$-$C_{13}$-alkenylene- or -alkinylene radical, and wherein A and B are optionally connected to one another via an O atom,
V represents a $CH_2$- or a C(O) group,
X is a direct bond between W and Y or is a straight-chain or branched-chain $C_1$-$C_{12}$- alkylene, $C_2$-$C_{12}$-alkenylene- or -alkinylene radical, in which
Y is
  1) a direct bond between X and Z, or
  2) when W is an $N^{30}(O^-)(R^6)$ group or an azolidinylene-N-oxide ring an $SO_n$-$R^{10}$ group, wherein n=0, 1 or 2, wherein $R^{10}$ represents a direct bond between $SO_n$ and Z or a straight-chain or branched-chain $C_1$-$C_6$-alkylene-, $C_2$-$C_6$-alkenylene- or -alkinylene radical, or 3) $R^{11}$ or O—$R^{11}$, wherein $R^{11}$ stands for
   i) a straight-chain or branched-chain $C_1$-$C_3$-alkylene-, $C_2$-$C_3$-alkenylene, or -alkinylene radical or for
   ii) an unsubstituted or substituted aryl radidal or heteroaryl radical or for
   iii) an unsubstituted or substituted $C_3$-$C_{10}$-cycloalkyl radical or for
   iv) an unsubstituted or substituted $C_4$-$C_{15}$-cycloalkylalkyl radical or for
   v) an unsubstituted or substituted $C_7$-$C_{20}$-aralkyl radical or for
   vi) an unsubstituted or substituted $C_1$-$C_6$-alkyl radical, or
4) CH=CF or
5) HN—C(O)—NH—$R^{12}$, wherein $R^{12}$ stands for an unsubstituted or substituted arylene radical, and wherein $R^{12}$ is bonded to Z, Z is a direct bond between Y and E or a straight-chain or branched-chain $C_1$-$C_9$-alkylene-, $C_2$-$C_9$-alkenylene- or -alkinylene radical, which is optionally partially or completely fluorinated, and E is a $CF_3$ group of an at least partially fluorinated aryl group, or a pharmacologically compatible acid addition salt or ester thereof.

26. An 17-Oxo-estratrienes with general formula III

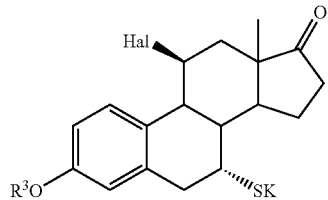

in which
Hal stands for F or Cl and is bonded in 11β-position,
$R^3$ stands for hydrogen, $C_1$-$C_4$-alkyl, $C_1$-$C_4$-alkanoyl or a cyclic $C_3$-$C_7$-ether with an O atom,
SK stands for the grouping U-V-W-X-Y-Z-E, which is bonded via U in 7α-position,
W stands for an $N^+(O)(R^6)$ group or for an azolidinylene-N-oxide ring, wherein the azolidinylene-N-oxide ring includes at least one C atom of grouping X,
$R^6$ is either H or $CH_2$-$R^7$ or C(O)-$R^7$,
$R^7$ is
   q) hydrogen or
   r) a straight-chain or branched-chain, non-fluorinated or at least partially fluorinated $C_1$-$C_{14}$-alkyl, $C_2$-$C_{14}$-alkenyl-or-alkinyl radical, any of which can be hydroxylated in one or more places and can be interrupted by one to three of the heteroatoms —O—,—S—and/or —$NR^9$, R-, in which $R^9$ stands for hydrogen or a $C_1$-$C_3$-alkyl radical, or
   s) an unsubstituted or substituted aryl- or heteroaryl radical or
   t) an unsubstituted or substituted $C_3$-$C_{10}$-cycloalkyl radical or
   u) an unsubstituted or substituted $C_4$-$C_{13}$-cycloalkylalkyl radical or
   v) an unsubstituted or substituted $C_7$-$C_{20}$-aralkyl radical or
   w) an unsubstituted or substituted heteroaryl-$C_1$-$C_6$-alkyl radical or
   x) an unsubstituted or substituted aminoalkyl radical or a biphenyl radical, U represents either a straight-chain or branched-chain $C_1$-$C_{13}$-alkylene, or $C_2$-$C_{13}$-alkenylene- or -alkinylene radical or the group A-B, wherein A is bonded in the 7α-position and represents a benzylidene radical that is bonded via -$CH_2$- in the 7α-position, a phenylene radical, or a $C_1$-$C_3$-alkylaryl radical that is bonded via the alkyl group in the 7α-position, and B stands for a straight-chained or branched-chain $C_1$-$C_{13}$-alkylene, or $C_2$-$C_{13}$-alkenylene- or -alkinylene radical, and wherein A and B are optionally connected to one another via an O atom, V represents a $CH_2$- or a C(O) group, X is a direct bond between W and Y or is a straight-chain or branched-chain $C_1$-$C_{12}$- alkylene, $C_2$-$C_{12}$-alkenylene- or -alkinylene radical, in which Y is
1) a direct bond between X and Z, or
2) when W is an $N^{30}(O^-)(R^6)$ group or an azolidinylene-N-oxide ring an $SO_n$-$R^{10}$ group, wherein n=0, 1 or 2, wherein $R^{10}$ represents a direct bond between $SO_n$ and Z or a straight-chain or branched-chain $C_1$-$C_6$-alkylene-, $C_2$-$C_6$-alkenylene- or -alkinylene radical, or
3) $R^{11}$ or O—$R^{11}$, wherein $R^{11}$ stands for
   i) a straight-chain or branched-chain $C_1$-$C_3$-alkylene-, $C_2$-$C_3$-alkenylene, or -alkinylene radical or for
   ii) an unsubstituted or substituted aryl radidal or heteroaryl radical or for
   iii) an unsubstituted or substituted $C_3$-$C_{10}$-cycloalkyl radical or for
   iv) an unsubstituted or substituted $C_4$-$C_{15}$-cycloalkylalkyl radical or for
   v) an unsubstituted or substituted $C_7$-$C_{20}$-aralkyl radical or for
   vi) an unsubstituted or substituted $C_1$-$C_6$-alkyl radical, or
4) CH=CF or
5) HN—C(O)—NH—$R^{12}$, wherein $R^{12}$ stands for an unsubstituted or substituted arylene radical, and wherein $R^{12}$ is bonded to Z, Z is a direct bond between Y and E or a straight-chain or branched-chain $C_1$-$C_9$-alkylene-, $C_2$-$C_9$-alkenylene- or -alkinylene radical, which is optionally partially or completely fluorinated, and E is a $CF_3$ group of an at least partially fluorinated aryl group, or a pharmacologically compatible acid addition salt or ester thereof.

27. A 17α-Alkyl-17β-oxy-estratriene of formula I

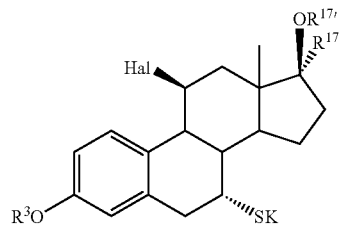

in which
- Hal stands for F or Cl, and is in 11β-position,
- $R^3$ stands for hydrogen, $C_1$-$C_4$-alkyl, $C_1$-$C_4$-alkanoyl or a cyclic $C_3$-$C_7$-ether with the O atom,
- $R^{17'}$ stands for hydrogen, $C_1$-$C_4$-alkyl or $C_1$-$C_4$-alkanoyl,
- $R^{17''}$ stands for $C_1$-$C_4$-alkyl, $C_1$-$C_4$-alkinyl, $C_1$-$C_4$-alkinyl as for at least partially fluorinated $C_1$-$C_4$-alkyl,
- wherein $R^{17'}$—O in 17β-position and $R^{17''}$ in 17α-position
- SK stands for U-V-W-X-Y-Z-E, which is bonded via U in 7α-position,
- U represents either a straight-chain or branched-chain $C_1$-$C_{13}$-alkylene, or $C_2$-$C_{13}$alkenylene- or -alkinylene radical or the group A-B, whereby A is bonded in the 7α-position and represents a benzylidene radical that is bonded via —CH$_2$— in the 7α-position, a phenylene radical, or a $C_1$-$C_3$-alkylaryl radical that is bonded via the alkyl group in the 7α-position, and B stands for a straight-chain or branched-chain $C_1$-$C_{13}$-alkylene, or $C_2$. $C_{13}$-alkenylene- or -alkinylene radical, and wherein A and B are optionally connected to one another via an O atom,
- V represents a CH$_2$— or a C(O) group,
- W is an $N(R^6)$— group or an $N^+(O^-)(R^6)$ group or an azolidinylene ring or an azolidinylene-N-oxide ring, wherein the azolidinylene ring or azolidinylene-N-oxide ring includes at least one C atom of grouping X,
- $R^6$ is either H or CH$_2$—$R^7$ or C(O)—$R^7$,
- $R^7$ is
  a) hydrogen or
  b) a straight-chain or branched-chain, non-fluorinated or at least partially fluorinated $C_1$-$C_{14}$-alkyl, $C_2$-$C_{14}$-alkenyl- or -alkinyl radical, any of which can be hydroxylated in one or more places and can be interrupted by one to three of the heteroatoms —O—, —S— and/or —$NR^9$—, in which $R^9$ stands for hydrogen or a $C_1$-$C_3$-alkyl radical, or
  c) an unsubstituted or substituted aryl- or heteroaryl radical or
  d) an unsubstituted or substituted $C_3$-$C_{10}$-cycloalkyl radical or
  e) an unsubstituted or substituted $C_4$-$C_{15}$-cycloalkylalkyl radical or
  f) an unsubstituted or substituted $C_7$-$C_{20}$-aralkyl radical or
  g) an unsubstituted or substituted heteroaryl-$C_1$-$C_6$-alkyl radical or
  h) an unsubstituted or substituted aminoalkyl radical or a biphenyl radical,
- X is a direct bond between W and Y or is a straight-chain or branched-chain $C_1$-$C_{12}$-alkylene, $C_2$-$C_{12}$-alkenylene- or -alkinylene radical, in which
- Y is
  1) a direct bond between X and Z, or
  2) when W is an $N^+(O^-)(R^6)$ group or an azolidinylene—N—oxide ring an $SO_n$—$R^{10}$ group, wherein n=0, 1 or 2, wherein $R^{10}$ represents a direct bond between $SO_n$ and Z or a straight-chain or branched-chain $C_1$-$C_6$-alkylene-, $C_2$-$C_6$-alkenylene- or -alkinylene radical, or
  3) $R^{11}$ or O—$R^{11}$, wherein $R^{11}$ stands for
    i) a straight-chain or branched-chain $C_1$-$C_5$-alkylene-, $C_2$-$C_5$-alkenylene- or -alkinylene radical or for
    ii) an unsubstituted or substituted aryl radical or heteroaryl radical or for
    iii) an unsubstituted or substituted $C_3$-$C_{10}$-cycloalkyl radical or for
    iv) an unsubstituted or substituted $C_4$-$C_{15}$-cycloalkylalkyl radical or for
    v) an unsubstituted or substituted $C_7$-$C_{20}$-aralkyl radical or for
    vi) an unsubstituted or substituted heteroaryl-$C_1$-$C_6$-alkyl radical, or
  4) CH=CF or
  5) HN—C(O)—NH—$R^{12}$, wherein $R^{12}$ stands for an unsubstituted or substituted arylene radical, and wherein $R^{12}$ is bonded to Z,
- Z is a direct bond between Y and E or a straight-chain or branched-chain $C_1$-$C_9$-alkylene-, $C_2$-$C_6$-alkenylene- or -alkinylene radical, which is optionally partially or completely fluorinated,
- E is a CF$_3$ group or an at least partially fluorinated aryl group, or a pharmacologically compatible acid addition salt or ester thereof.

* * * * *

UNITED STATES PATENT AND TRADEMARK OFFICE
CERTIFICATE OF CORRECTION

PATENT NO. : 7,538,100 B2
APPLICATION NO. : 11/188992
DATED : May 26, 2009
INVENTOR(S) : Bohlmann et al.

It is certified that error appears in the above-identified patent and that said Letters Patent is hereby corrected as shown below:

Column 23, line 33 reads, "A 17β-Alkyl-17β-oxy-estratrienes of formula 1" SHOULD READ --A 17α-Alkyl-17β-oxy-estratriene of formula 1--

Column 23, line 54 reads, "$R^{17''}$ stands for $C_1$-$C_4$-alkyl, $C_1$-$C_4$-alkinyl $C_1$-$C_4$-alkinyl" SHOULD READ --$R^{17''}$ stands for $C_1$-$C_4$-alkyl, $C_2$-$C_4$-alkinyl--

Column 23, line 55 reads, "as for at least partially fluorinated $C_1$-$C_4$-alkyl," SHOULD READ --or for at least partially fluorinated $C_1$-$C_4$-alkyl,--

Column 23, line 60 reads, "$C_1$-$C_{13}$-alkylene alkenylene- or –alkinylene radical or" SHOULD READ --$C_1$-$C_{13}$-alkylene or $C_2$-$C_{13}$- alkenylene- or –alkinylene radical or--

Column 25, line 21 reads, "An estratrienes according to claim 1, wherein $R^3$ stands" SHOULD READ --An estratriene according to claim 1, wherein $R^3$ stands--

Column 25, line 24 reads, "An estratrienes according to claim 1, wherein $R^{17'}$ stands" SHOULD READ --An estratriene according to claim 1, wherein $R^{17'}$ stands--

Column 25, line 27 reads, "An estratrienes according to claim 1, wherein Hal stands" SHOULD READ --An estratriene according to claim 1, wherein Hal stands--

Column 25, line 29 reads, "An estratrienes according to claim 1, wherein U stands" SHOULD READ --An estratriene according to claim 1, wherein U stands--

Column 25, line 30 reads, "for $(CH_2)_p$, whereby p is an integer from 2 to 10." SHOULD READ --for $(CH_2)_p$, wherein p is an integer from 2 to 10.--

Column 25, line 31 reads, "An estratrienes according to claim 5, wherein p=4." SHOULD READ --An estratriene according to claim 5, wherein p=4.--

Signed and Sealed this
Thirteenth Day of March, 2012

David J. Kappos
*Director of the United States Patent and Trademark Office*

CERTIFICATE OF CORRECTION (continued)
U.S. Pat. No. 7,538,100 B2

Column 25, line 32 reads, "An estratrienes according to claim 1, wherein V stands" SHOULD READ --An estratriene according to claim 1, wherein V stands--

Column 25, line 34 reads, "An estratrienes according to claim 1, wherein W stands" SHOULD READ --An estratriene according to claim 1, wherein W stands--

Column 25, line 35 reads, "for $N(R^6)$— or $N^+(O^-)(R^6)$, whereby $R^6$ is hydrogen or a" SHOULD READ --for $N(R^6)$— or $N^+(O^-)(R^6)$, wherein $R^6$ is hydrogen or a--

Column 25, line 37 reads, "An estratrienes according to claim 1, wherein $R^6$ stands" SHOULD READ --estratriene according to claim 1, wherein $R^6$ stands--

Column 25, line 39 reads, "An estratrienes according to claim 1, wherein X stands" SHOULD READ --An estratriene according to claim 1, wherein X stands--

Column 25, line 41 reads, "An estratrienes according to claim 1, wherein Y is a" SHOULD READ --An estratriene according to claim 1, wherein Y is a--

Column 25, line 42 reads, "direct bond between X and Z or an $SO_n$ group, whereby n=0," SHOULD READ --direct bond between X and Z or an $SO_n$ group, whereIN n=0,--

Column 25, line 44 reads, "An estratrienes according to claim 1, wherein Z is a" SHOULD READ --An estratriene according to claim 1, wherein Z is a--

Column 25, line 47 reads, "An estratrienes according to claim 1, wherein E stands" SHOULD READ --An estratriene according to claim 1, wherein E stands--

Column 25, line 49 reads, "An estratrienes according to claim 1, wherein Z-E" SHOULD READ --An estratriene according to claim 1, wherein Z-E--

Column 25, line 51 reads, "An estratrienes, which is" SHOULD READ --An estratriene, which is--

Column 26, line 23 reads, "(7,7,8,8,9,9,10,10,10-nonafluorodecyl)amino]pentyl}-11β-" SHOULD READ --(7,7,8,8,9,9,10,10,10-nonafluorodecyl)amino]pentyl}-17α--

Column 27, line 38 reads, "17β-Oxy-estratrienes of formula II" SHOULD READ --A 17β-Oxy-estratriene of formula II--

Column 27, line 56 reads, "SK stands for the grouping U-V-W-X-Y-Z-E, which is" SHOULD READ --stands for U-V-W-X-Y-Z-E, which is--

Column 28, line 36 reads, "m) an unsubstituted $C_4$-$C_{13}$-cycloalkyla-" SHOULD READ --m) an unsubstituted $C_4$-$C_{15}$-cycloalkyla- --

CERTIFICATE OF CORRECTION (continued)
U.S. Pat. No. 7,538,100 B2

Column 28, line 62 reads, "2) when W is an $N^{30}$ ($O^-$)($R^6$) group or an azolidinylene-" SHOULD READ --2) when W is an $N^+$ ($O^-$)($R^6$) group or an azolidinylene- --

Column 29, line 27 reads, "An 17-Oxo-estrarienes with general formula III" SHOULD READ --An 17-Oxo-estrariene with general formula III--

Column 29, line 58 reads, "S-and/or-$NR^9$, R-, in which $R^9$ stands for hydro-" SHOULD READ --S-and/or-$NR^9$-, in which $R^9$ stands for hydro- --

Column 30, line 22 reads, "2) when W is an $N^{30}$($O^-$)($R^6$) group or an azolidinylene-" SHOULD READ --2) when W is an $N^+$($O^-$)($R^6$) group or an azolidinylene- --

Column 30, line 29 reads, "i) a straight-chain or branched-chain $C_1$-$C_3$-alkyl-" SHOULD READ --i) a straight-chain or branched-chain $C_1$-$C_5$-alkyl- --

Column 30, line 30 reads, "lene- $C_2$-$C_3$-alkenylene, or -alkinylene radical or" SHOULD READ --lene-$C_2$-$C_5$-alkenylene, or -alkinylene radical or--

Column 31, line 6 reads, "$R^{17''}$ stands for $C_1$-$C_4$-alkyl, $C_1$-$C_4$-alkinyl, $C_1$-$C_4$-alkinyl" SHOULD READ --$R^{17''}$ stands for $C_1$-$C_4$-alkyl, alkenyl, $C_2$-$C_4$-alkinyl--

Column 31, line 7 reads, "as for at least partially fluorinated $C_1$-$C_4$-alkyl," SHOULD READ --or for at least partially fluorinated $C_1$-$C_4$-alkyl, --

Column 31, line 13 reads, "radical or the group A-B whereby A is bonded in the" SHOULD READ --radical or the group A-B wherein A is bonded in the--